US012584167B2

(12) United States Patent
Saito et al.

(10) Patent No.: US 12,584,167 B2
(45) Date of Patent: Mar. 24, 2026

(54) METHOD FOR AMPLIFYING NUCLEOTIDE SEQUENCE AND SEQUENCE DETERMINATION

(71) Applicants: JAPAN INSTITUTE FOR HEALTH SECURITY, Tokyo (JP); FASMAC CO., LTD, Atsugi (JP)

(72) Inventors: Masumichi Saito, Musashimurayama (JP); Haruka Momose, Musashimurayama (JP); Yusaku Wada, Atsugi (JP); Takahiro Matsudaira, Atsugi (JP)

(73) Assignees: JAPAN INSTITUTE FOR HEALTH SECURITY, Tokyo (JP); FASMAC CO., LTD, Kanagawa (JP)

( * ) Notice: Subject to any disclaimer, the term of this patent is extended or adjusted under 35 U.S.C. 154(b) by 925 days.

(21) Appl. No.: 17/636,591

(22) PCT Filed: Aug. 14, 2020

(86) PCT No.: PCT/JP2020/030907
§ 371 (c)(1),
(2) Date: Feb. 18, 2022

(87) PCT Pub. No.: WO2021/033648
PCT Pub. Date: Feb. 25, 2021

(65) Prior Publication Data
US 2023/0193373 A1      Jun. 22, 2023

(30) Foreign Application Priority Data
Aug. 20, 2019      (JP) ................................. 2019-150535

(51) Int. Cl.
C12Q 1/6865      (2018.01)
C12Q 1/6848      (2018.01)
C12Q 1/6869      (2018.01)

(52) U.S. Cl.
CPC ......... *C12Q 1/6865* (2013.01); *C12Q 1/6848* (2013.01); *C12Q 1/6869* (2013.01)

(58) Field of Classification Search
None
See application file for complete search history.

(56) References Cited

U.S. PATENT DOCUMENTS

| | | |
|---|---|---|
| 2012/0258867 A1 | 10/2012 | Cao et al. |
| 2018/0195119 A1 | 7/2018 | Liu et al. |

FOREIGN PATENT DOCUMENTS

| | | |
|---|---|---|
| JP | 2002-502605 A | 1/2002 |
| JP | 2004-275037 A | 10/2004 |

(Continued)

OTHER PUBLICATIONS

Spalinskas et al. LT-RADE: An Efficient User-Friendly Genome Walking Method Applied to the Molecular Characterization of the Insertion Site of Genetically Modified Maize MON810 and Rice LLRICE62. Food Anal. Methods 6:705-712. (Year: 2013).*

(Continued)

*Primary Examiner* — Samuel C Woolwine
(74) *Attorney, Agent, or Firm* — Sughrue Mion, PLLC

(57)      ABSTRACT

The present invention provides a method for amplifying a sequence adjacent to a specific sequence, comprising the steps of: annealing a first forward primer to the specific sequence to synthesize a complementary strand; sequentially polymerically adding a first deoxynucleotide and a second deoxynucleotide to a 3'-end of the complementary strand; annealing a first reverse primer to a binding site between the 3'-end of the complementary strand and a polydeoxynucleotide strand composed of the first deoxynucleotide to synthesize a double-stranded DNA; performing a PCR with the double-stranded DNA as a template by using a second forward primer complementary to the specific sequence and a first reverse primer; and further per- (Continued)

forming a PCR by using a third forward primer complementary to the specific sequence and a second reverse primer.

5 Claims, 7 Drawing Sheets

Specification includes a Sequence Listing.

(56)                    References Cited

FOREIGN PATENT DOCUMENTS

| | | | |
|----|----------------|-----|---------|
| JP | 2006-166907 | A | 6/2006 |
| JP | 2014-511695 | A | 5/2014 |
| JP | 2020-005549 | A | 1/2020 |
| WO | 2012/138549 | A1 | 10/2012 |
| WO | 2013/112923 | A1 | 8/2013 |
| WO | 2015/111209 | A1 | 7/2015 |

OTHER PUBLICATIONS

Shunsuke Yamauchi, et al., "Development of a method in clonality analysis of HTLV-1 (RAIS1) for next-generation", Journal of the Japanese Society for Laboratory Hematology, Jun. 22, 2020, 01-17-3, entire text, non-official translation, vol. 21, supplement, S160.

Taian Liu, et al., "A tailing genome walking method suitable for genomes with high local GC content", Analytical Biochemistry, 2013, p. 101-103, vol. 441.

Anna Paruzynski, et al., "Genome-wide high-throughput integrome analyses by nrLAM-PCR and next-generation sequencing", Nature Protocols, Aug. 2010, pp. 1379-1395, vol. 5, No. 8.

Knut Rudi, et al., "Restriction Cutting Independent Method for Cloning Genomic DNA Segments Outside the Boundaries of Known Sequences", Biotechniques, 1999, pp. 1170-1172, 1176-1177, vol. 27.

Masumichi Saito, et al., "A high-throughput detection method for the clonality of Human T-cell leukemia virus type-1 infected cells in vivo", International Journal of Hematology, Jul. 29, 2020, pp. 300-306, vol. 112.

Saeko Tanaka, et al., "Application of a detection method of transgene integration sites in plants", Abstracts of the 249th meeting of CSSJ, Mar. 26, 2020, p. 88.

International Search Report for PCT/JP2020/030907 dated Oct. 20, 2020 [PCT/ISA/210].

Written Opinion for PCT/JP2020/030907 dated Oct. 20, 2020 [PCT/ISA/237].

Extended European Search Report issued Sep. 1, 2023 in European Application No. 20854353.8.

Communication, dated Mar. 3, 2022, issued by the International Bureau in International Application No. PCT/JP2020/030907.

* cited by examiner

SEQUENCE LISTING

```
<160> NUMBER OF SEQ ID NOS: 53

<210> SEQ ID NO 1
<211> LENGTH: 38
<212> TYPE: DNA
<213> ORGANISM: Artificial Sequence
<220> FEATURE:
<223> OTHER INFORMATION: Synthetic sequence, Poly-A (T) G tail

<400> SEQUENCE: 1
aaaaaaaaaa aaaaaaaaaa aaaaagaag ggaggggg                          38

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence, ADP1

<400> SEQUENCE: 2
acagcaggtc agtcaagcag ta                                          22

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence, ADP2

<400> SEQUENCE: 3
agcagtagca gcagttcgat aa                                          22

<210> SEQ ID NO 4
<211> LENGTH: 17
<212> TYPE: DNA
<213> ORGANISM: Artificial Sequence
<220> FEATURE:
<223> OTHER INFORMATION: Synthetic sequence, M13-20

<400> SEQUENCE: 4
gtaaaacgac ggccagt                                                17

<210> SEQ ID NO 5
<211> LENGTH: 18
<212> TYPE: DNA
<213> ORGANISM: Artificial Sequence
<220> FEATURE:
<223> OTHER INFORMATION: Synthetic sequence, M13-21

<400> SEQUENCE: 5
tgtaaaacga cggccagt                                               18

<210> SEQ ID NO 6
<211> LENGTH: 24
<212> TYPE: DNA
<213> ORGANISM: Artificial Sequence
```

-continued

```
<220> FEATURE:
<223> OTHER INFORMATION: Synthetic sequence, M13-47

<400> SEQUENCE: 6
cgccagggtt ttcccagtca cgac                                          24

<210> SEQ ID NO 7
<211> LENGTH: 17
<212> TYPE: DNA
<213> ORGANISM: Artificial Sequence
<220> FEATURE:
<223> OTHER INFORMATION: Synthetic sequence, M13-P5

<400> SEQUENCE: 7
caggaaacag ctatgac                                                  17

<210> SEQ ID NO 8
<211> LENGTH: 24
<212> TYPE: DNA
<213> ORGANISM: Artificial Sequence
<220> FEATURE:
<223> OTHER INFORMATION: Synthetic sequence, M13rev

<400> SEQUENCE: 8
gagcggataa caatttcaca cagg                                          24

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence, T3

<400> SEQUENCE: 9
attaaccctc actaaaggga a                                             21

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence, T3pro

<400> SEQUENCE: 10
attaaccctc actaaaggga                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence, T7

<400> SEQUENCE: 11
taatacgact cactataggg                                               20

<210> SEQ ID NO 12
<211> LENGTH: 19
<212> TYPE: DNA
<213> ORGANISM: Artificial Sequence
<220> FEATURE:
<223> OTHER INFORMATION: Synthetic sequence, T7term

<400> SEQUENCE: 12
gctagttatt gctcagcgg                                                19
```

-continued

```
<210> SEQ ID NO 13
<211> LENGTH: 18
<212> TYPE: DNA
<213> ORGANISM: Artificial Sequence
<220> FEATURE:
<223> OTHER INFORMATION: Synthetic sequence, BGHrev

<400> SEQUENCE: 13
tagaaggcac agtcgagg                                                    18

<210> SEQ ID NO 14
<211> LENGTH: 24
<212> TYPE: DNA
<213> ORGANISM: Artificial Sequence
<220> FEATURE:
<223> OTHER INFORMATION: Synthetic sequence, SP6

<400> SEQUENCE: 14
catacgattt aggtgacact atag                                             24

<210> SEQ ID NO 15
<211> LENGTH: 22
<212> TYPE: DNA
<213> ORGANISM: Artificial Sequence
<220> FEATURE:
<223> OTHER INFORMATION: Synthetic sequence, SP6-II

<400> SEQUENCE: 15
atttaggtga cactatagaa ta                                               22

<210> SEQ ID NO 16
<211> LENGTH: 19
<212> TYPE: DNA
<213> ORGANISM: Artificial Sequence
<220> FEATURE:
<223> OTHER INFORMATION: Synthetic sequence, SP6pro

<400> SEQUENCE: 16
gatttaggtg acactatag                                                   19

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence, HTLV-F1

<400> SEQUENCE: 17
caaggcctac cacccctcat                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic sequence, HTLV-F2

<400> SEQUENCE: 18
cctgaccctg cttgctcaac                                                  20

<210> SEQ ID NO 19
<211> LENGTH: 21
<212> TYPE: DNA
<213> ORGANISM: Artificial Sequence
<220> FEATURE:
<223> OTHER INFORMATION: Synthetic sequence, HTLV-F3
```

-continued

<400> SEQUENCE: 19
gccagcgaca gcccatycta t                                                  21

<210> SEQ ID NO 20
<211> LENGTH: 23
<212> TYPE: DNA
<213> ORGANISM: Artificial Sequence
<220> FEATURE:
<223> OTHER INFORMATION: Synthetic sequence, HIV-F1

<400> SEQUENCE: 20
cctggctgga agcacaagag gag                                                23

<210> SEQ ID NO 21
<211> LENGTH: 22
<212> TYPE: DNA
<213> ORGANISM: Artificial Sequence
<220> FEATURE:
<223> OTHER INFORMATION: Synthetic sequence, HIV-F2

<400> SEQUENCE: 21
gggactttcc agggaggtgt gg                                                 22

<210> SEQ ID NO 22
<211> LENGTH: 23
<212> TYPE: DNA
<213> ORGANISM: Artificial Sequence
<220> FEATURE:
<223> OTHER INFORMATION: Synthetic sequence, HIV-F3

<400> SEQUENCE: 22
gcccgtctgt tgtgtgactc tgg                                                23

<210> SEQ ID NO 23
<211> LENGTH: 24
<212> TYPE: DNA
<213> ORGANISM: Artificial Sequence
<220> FEATURE:
<223> OTHER INFORMATION: Synthetic sequence, SIV-F1

<400> SEQUENCE: 23
tcagtgaggc caaaagttcc ccta                                               24

<210> SEQ ID NO 24
<211> LENGTH: 23
<212> TYPE: DNA
<213> ORGANISM: Artificial Sequence
<220> FEATURE:
<223> OTHER INFORMATION: Synthetic sequence, SIV-F2

<400> SEQUENCE: 24
gagcctgggt gttccctgct aga                                                23

<210> SEQ ID NO 25
<211> LENGTH: 23
<212> TYPE: DNA
<213> ORGANISM: Artificial Sequence
<220> FEATURE:
<223> OTHER INFORMATION: Synthetic sequence, SIV-F3

<400> SEQUENCE: 25
cgcctggtca actcggtact caa                                                23

<210> SEQ ID NO 26

```
<211> LENGTH: 23
<212> TYPE: DNA
<213> ORGANISM: Artificial Sequence
<220> FEATURE:
<223> OTHER INFORMATION: Synthetic sequence, HBV-F1

<400> SEQUENCE: 26
gccaggtctg tgccaagtgt ttg                                              23

<210> SEQ ID NO 27
<211> LENGTH: 23
<212> TYPE: DNA
<213> ORGANISM: Artificial Sequence
<220> FEATURE:
<223> OTHER INFORMATION: Synthetic sequence, HBV-F2

<400> SEQUENCE: 27
tctgtgccaa gtgtttgctg acg                                              23

<210> SEQ ID NO 28
<211> LENGTH: 21
<212> TYPE: DNA
<213> ORGANISM: Artificial Sequence
<220> FEATURE:
<223> OTHER INFORMATION: Synthetic sequence, HBV-F3

<400> SEQUENCE: 28
cactggctgg ggcttggtca t                                                21

<210> SEQ ID NO 29
<211> LENGTH: 23
<212> TYPE: DNA
<213> ORGANISM: Artificial Sequence
<220> FEATURE:
<223> OTHER INFORMATION: Synthetic sequence, ADV-F1

<400> SEQUENCE: 29
ctgaaatgtg tgggcgtggc tta                                              23

<210> SEQ ID NO 30
<211> LENGTH: 23
<212> TYPE: DNA
<213> ORGANISM: Artificial Sequence
<220> FEATURE:
<223> OTHER INFORMATION: Synthetic sequence, ADV-F2

<400> SEQUENCE: 30
ctgcggggtg gtgttgtaga tga                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic sequence, ADV-F3

<400> SEQUENCE: 31
ctgggcgtgg tgcctaaaaa tgt                                              23

<210> SEQ ID NO 32
<211> LENGTH: 23
<212> TYPE: DNA
<213> ORGANISM: Artificial Sequence
<220> FEATURE:
<223> OTHER INFORMATION: Synthetic sequence, ldlr-LoxP-F1
```

<400> SEQUENCE: 32 gaaaggggt ttgaatggtg tgg                                                         23

<210> SEQ ID NO 33
<211> LENGTH: 23
<212> TYPE: DNA
<213> ORGANISM: Artificial Sequence
<220> FEATURE:
<223> OTHER INFORMATION: Synthetic sequence, ldlr-LoxP-F2

<400> SEQUENCE: 33
tgaggggtgg tctagcctga tgg                                                        23

<210> SEQ ID NO 34
<211> LENGTH: 24
<212> TYPE: DNA
<213> ORGANISM: Artificial Sequence
<220> FEATURE:
<223> OTHER INFORMATION: Synthetic sequence, ldlr-LoxP-F3

<400> SEQUENCE: 34
tgggcacact gaagaggaca aagt                                                       24

<210> SEQ ID NO 35
<211> LENGTH: 22
<212> TYPE: DNA
<213> ORGANISM: Artificial Sequence
<220> FEATURE:
<223> OTHER INFORMATION: Synthetic sequence, Bt176-F1

<400> SEQUENCE: 35
cttcaccacc cccttcaact tc                                                         22

<210> SEQ ID NO 36
<211> LENGTH: 22
<212> TYPE: DNA
<213> ORGANISM: Artificial Sequence
<220> FEATURE:
<223> OTHER INFORMATION: Synthetic sequence, Bt176-F2

<400> SEQUENCE: 36
agtacgacct ggagagggct ca                                                         22

<210> SEQ ID NO 37
<211> LENGTH: 22
<212> TYPE: DNA
<213> ORGANISM: Artificial Sequence
<220> FEATURE:
<223> OTHER INFORMATION: Synthetic sequence, Bt176-F3

<400> SEQUENCE: 37
aagaccgacg tgaccgacta cc                                                         22

<210> SEQ ID NO 38
<211> LENGTH: 20
<212> TYPE: DNA
<213> ORGANISM: Artificial Sequence
<220> FEATURE:
<223> OTHER INFORMATION: Synthetic sequence, Sanger seq primer

<400> SEQUENCE: 38
acactctttc cctacacgac                                                            20

<210> SEQ ID NO 39

-continued

```
<211> LENGTH: 59
<212> TYPE: DNA
<213> ORGANISM: Artificial Sequence
<220> FEATURE:
<223> OTHER INFORMATION: Synthetic sequence, NGS-F2
<220> FEATURE:
<221> NAME/KEY: misc_feature
<222> LOCATION: (30)..(37)
<223> OTHER INFORMATION: n is a, c, g, or t

<400> SEQUENCE: 39
aatgatacgg cgaccaccga gatctacacn nnnnnnaca ctctttccct acacgacgc          59

<210> SEQ ID NO 40
<211> LENGTH: 33
<212> TYPE: DNA
<213> ORGANISM: Artificial Sequence
<220> FEATURE:
<223> OTHER INFORMATION: Synthetic sequence, illumina read1 primer
      region

<400> SEQUENCE: 40
acactctttc cctacacgac gctcttccga tct                                    33

<210> SEQ ID NO 41
<211> LENGTH: 25
<212> TYPE: DNA
<213> ORGANISM: Artificial Sequence
<220> FEATURE:
<223> OTHER INFORMATION: Synthetic sequence, Oligo-dT(23) iOligo-dT-AD2j
<220> FEATURE:
<221> NAME/KEY: misc_feature
<222> LOCATION: (25)..(25)
<223> OTHER INFORMATION: n is a, c, g, or t

<400> SEQUENCE: 41
tttttttttt tttttttttt tttvn                                             25

<210> SEQ ID NO 42
<211> LENGTH: 24
<212> TYPE: DNA
<213> ORGANISM: Artificial Sequence
<220> FEATURE:
<223> OTHER INFORMATION: Synthetic sequence, Oligo-dT-AD3

<400> SEQUENCE: 42
tttttttttt tttttttttt tttv                                              24

<210> SEQ ID NO 43
<211> LENGTH: 23
<212> TYPE: DNA
<213> ORGANISM: Artificial Sequence
<220> FEATURE:
<223> OTHER INFORMATION: Synthetic sequence, Oligo-dT-AD4

<400> SEQUENCE: 43
tttttttttt tttttttttt ttt                                               23

<210> SEQ ID NO 44
<211> LENGTH: 54
<212> TYPE: DNA
<213> ORGANISM: Artificial Sequence
<220> FEATURE:
<223> OTHER INFORMATION: Synthetic sequence, NGS-R2
<220> FEATURE:
<221> NAME/KEY: misc_feature
<222> LOCATION: (25)..(32)
<223> OTHER INFORMATION: n is a, c, g, or t
```

-continued

```
<400> SEQUENCE: 44
caagcagaag acggcatacg agatnnnnnn nngtgactgg agttcagacg tgtg          54

<210> SEQ ID NO 45
<211> LENGTH: 34
<212> TYPE: DNA
<213> ORGANISM: Artificial Sequence
<220> FEATURE:
<223> OTHER INFORMATION: Synthetic sequence, illumina read2 primer
      region

<400> SEQUENCE: 45
gtgactggag ttcagacgtg tgctcttccg atct                               34

<210> SEQ ID NO 46
<211> LENGTH: 18
<212> TYPE: DNA
<213> ORGANISM: Artificial Sequence
<220> FEATURE:
<223> OTHER INFORMATION: Synthetic sequence, TCRA-F1

<400> SEQUENCE: 46
ggctggggaa gaaggtgt                                                 18

<210> SEQ ID NO 47
<211> LENGTH: 23
<212> TYPE: DNA
<213> ORGANISM: Artificial Sequence
<220> FEATURE:
<223> OTHER INFORMATION: Synthetic sequence, TCRA-F2

<400> SEQUENCE: 47
atgctgttgt tgaaggcgtt tgc                                           23

<210> SEQ ID NO 48
<211> LENGTH: 24
<212> TYPE: DNA
<213> ORGANISM: Artificial Sequence
<220> FEATURE:
<223> OTHER INFORMATION: Synthetic sequence, TCRA-F3

<400> SEQUENCE: 48
tcggtgaata ggcagacaga cttg                                          24

<210> SEQ ID NO 49
<211> LENGTH: 20
<212> TYPE: DNA
<213> ORGANISM: Artificial Sequence
<220> FEATURE:
<223> OTHER INFORMATION: Synthetic sequence, TCRB-F1

<400> SEQUENCE: 49
gcccgtagaa ctggacttga                                               20

<210> SEQ ID NO 50
<211> LENGTH: 22
<212> TYPE: DNA
<213> ORGANISM: Artificial Sequence
<220> FEATURE:
<223> OTHER INFORMATION: Synthetic sequence, TCRB-F2

<400> SEQUENCE: 50
gctcaggcag tatctggagt ca                                            22

<210> SEQ ID NO 51
```

-continued

```
<211> LENGTH: 20
<212> TYPE: DNA
<213> ORGANISM: Artificial Sequence
<220> FEATURE:
<223> OTHER INFORMATION: Synthetic sequence, TCRB-F3

<400> SEQUENCE: 51
cagtgtggcc ttttgggtgt                                                          20

<210> SEQ ID NO 52
<211> LENGTH: 38
<212> TYPE: DNA
<213> ORGANISM: Artificial Sequence
<220> FEATURE:
<223> OTHER INFORMATION: Synthetic sequence

<400> SEQUENCE: 52
aaaaaaaaaa aaaaaaaaaa aaaaagaag ggaggggg                                       38

<210> SEQ ID NO 53
<211> LENGTH: 14
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: n is a, c, g, or t

<400> SEQUENCE: 53
nvtttttttt tttt                                                                14
```

METHOD FOR AMPLIFYING NUCLEOTIDE SEQUENCE AND SEQUENCE DETERMINATION

CROSS REFERENCE TO RELATED APPLICATIONS

This application is a National Stage of International Application No. PCT/JP2020/030907 filed Aug. 14, 2020, claiming priority based on Japanese Patent Application No. 2019-150535 filed Aug. 20, 2019.

TECHNICAL FIELD

The present invention relates to a nucleotide sequence amplification method and a sequencing method. More specifically, the present invention relates to a method for amplifying a sequence adjacent to a specific sequence and a method for determining the sequence, for example, a method for amplifying the sequence at the insertion site (adjacent sequence) of foreign DNA (specific sequence) inserted into a host genome and determining the sequence. Further, for example, the present invention relates to a method for amplifying a variable region sequence (adjacent sequence) adjacent to a constant region sequence (specific sequence) and determining the sequence in RNA encoding a T-cell receptor (TCR) or the like. Moreover, the present invention relates to a kit for carrying out these methods.

BACKGROUND ART

Gene therapy using retroviral vectors and lentiviral vectors has already acquired many achievements, and further research and development and clinical trials are underway. However, in this therapeutic method, a viral vector may be integrated at an unintended position on the chromosome (host genome) to be treated. If this insertion enters the vicinity of an oncogene or a tumor suppressor gene, it may become cancerous. In the example of gene therapy targeting hematopoietic stem cells for congenital immunodeficiency using retroviral vectors, while it has been shown to be effective, there are cases in which 11 out of 92 patients developed leukemia and one of them died. Therefore, in such gene therapy, 15 years of subject follow-up is required as a safety assurance measure.

Further, in recent years, gene modification technology has been rapidly developing with the rise of genome editing. However, in a genome editing technique (so-called SDN-3) in which a foreign DNA or the like is introduced and sandwiched between sequences homologous to the target site and the DNA or the like is inserted site-specifically by homologous recombination, there are problems such as the introduction of the aforementioned DNA or the like into an unintended site (off-target mutation), and its use in the medical field requires special care.

In addition, it has been suggested that even in diseases related to viruses such as HTLV-1, there is a relationship between the insertion site into the host genome and the pathological condition. For example, while carriers have a high frequency of virus-derived DNA embedded in genomic regions where transcription is originally inactivated, patients with virus-associated diseases (such as ATL) are known to have such DNA embedded near the transcription start site. Therefore, it is extremely important to properly identify the insertion position in the host genome in effectively and appropriately determining the risk of developing a virus-related disease.

As above, in gene therapy using viral vectors and genome editing technique, gene modification technology by genome editing or the like, and virus-related diseases, it is desired to identify the insertion site of foreign DNA on the host genome.

However, the insertion site of foreign DNA on the host genome, especially the position of random integration, is unknown, and its identification is difficult. Primitive methods include mate pair sequences for the entire genome, but this method is insensitive due to lack of selectivity and is costly. Also, various methods have been developed for the identification of DNA sequences near the insertion site of foreign DNA, and examples include a method in which genomic DNA is fragmented and cycled by ligation, and then subjected to inverse PCR with a foreign DNA-specific oligonucleotide, and others include Tail-PCR, LAM-PCR, nrLAM-PCR (PTL 1 and NPL 1), and the like. However, these are inadequate in terms of time required, operability, efficiency, sensitivity and cost.

CITATION LIST

Patent Literature

[PTL 1] International Publication No. WO2012/138549

Non Patent Literature

[NPL 1] Paruzynski A. et al., Nat Protoc., 2010 August, Vol. 5, Issue 8, pp. 1379 to 1395

SUMMARY OF INVENTION

Technical Problem

The present invention has been made in view of the above-mentioned problems of the related art, and an object thereof is to provide a method that enables a method for amplifying a sequence adjacent to a specific sequence. For example, an object of the present invention is to provide a method capable of amplifying a sequence at an insertion site of a foreign DNA (specific sequence) inserted into a host genome (sequence adjacent to a specific sequence).

Solution to Problem

The present inventors have made earnest studies to achieve the above object, and have found as a result that a sequence adjacent to a specific sequence in a DNA strand can be amplified by a method including steps 1 to 6 as shown in FIG. 1.

In nrLAM-PCR, which requires the shortest time in the conventional methods, for example, as described in NPL 1, it takes 30 hours or more to obtain an amplification product of a sequence adjacent to a specific sequence ("TIMING" on page 1392 of NPL 1 shows that the cumulative time from Steps 1-3, Linear PCR to Steps 32 and 33, Second exponential PCR is 32.5 hours). However, the aforementioned method makes it possible to obtain the product in about 3 hours, and has a short time required and high efficiency, as shown in FIG. 2.

Further, in nrLAM-PCR, for example, as described in PTL 1 and NPL 1, the purification step requires a substance other than nucleotides such as biotin and streptavidin, which is costly. On the other hand, in the aforementioned method, since it is sufficient to have a primer composed only of nucleotides, it is also excellent in terms of cost.

Further, as described in NPL 1, in nrLAM-PCR, the linker ligation reaction does not proceed 100%, so that the sensitivity is low (see NPL 1, page 1379, right column, lines 24 to 27). On the other hand, according to the aforementioned method, as shown in Examples described later, in the case of analyzing a mixture of the genomic DNA of infected cells inserted with one copy of HTLV-1 and the genomic DNA of uninfected cells, adjusted to a predetermined proviral level, it is possible to obtain a specific amplification product even when the proviral level is as small as 0.032%, and adjacent sequences can be detected with high sensitivity.

In addition, the aforementioned method is highly versatile because it allows specific amplification of the insertion site of each foreign DNA, not only in HTLV-1, but also in any of genomic DNA in which HIV-1, SIV, HBV, and adenovirus are each inserted, genomic DNA of cells that are off-target in genome editing, and genomic DNA of genetically modified plant cells.

Furthermore, even when the genomic DNAs of three HTLV-1 carrier samples are used and independently reacted and analyzed twice, the same amplification product can be obtained and the reproducibility is high.

Further, the method including steps 1 to 6 as shown in FIG. 1 makes it possible to amplify the variable region sequence (adjacent sequence) adjacent to the constant region sequence (specific sequence) in the RNA strand encoding the T-cell receptor (TCR) or the like, and to determine the sequence. That is, regardless of whether it is a DNA strand or an RNA strand, a sequence adjacent to a specific sequence in the nucleotide strand can be amplified.

The present invention is based on the above results, and relates to a method for amplifying a sequence adjacent to a specific sequence and a method for determining the sequence. The present invention also relates to a kit for carrying out these methods, and more specifically to the following invention.

<1> A method for amplifying a sequence adjacent to a specific sequence in a nucleotide strand, comprising the following steps (1) to (6):

(1) a step of annealing a first forward primer to the specific sequence, performing an extension reaction with the primer as a starting point, and synthesizing a complementary strand containing a sequence complementary to the adjacent sequence at a 3'-end;

(2) a step of polymerically adding a first deoxynucleotide to the 3'-end of the complementary strand obtained in step (1);

(3) a step of further polymerically adding a second deoxynucleotide to a 3'-end of a polydeoxynucleotide strand composed of the first deoxynucleotide added in step (2);

(4) a step of annealing a first reverse primer to a binding site between the 3'-end of the complementary strand and the polydeoxynucleotide strand in a single-stranded DNA formed in step (3), performing an extension reaction with the primer as a starting point, and synthesizing a double-stranded DNA;

(5) a step of performing a polymerase chain reaction with the double-stranded DNA synthesized in step (4) as a template by using a second forward primer complementary to the specific sequence and a first reverse primer; and (6) a step of further performing a polymerase chain reaction with an amplification product obtained in step (5) as a template by using a third forward primer complementary to the specific sequence and a second reverse primer, wherein the second forward primer is located closer to the adjacent sequence than the first forward primer in the specific sequence, the third forward primer is located closer to the adjacent sequence than the second forward primer in the specific sequence, the first reverse primer is a primer containing an adapter primer sequence and an oligonucleotide composed of a third deoxynucleotide in order from a 5'-end, the second reverse primer is a primer containing an adapter primer sequence at the 3'-end, the first to third deoxynucleotides are a first deoxynucleotide, each selected from four types consisting of deoxyadenosine, deoxyguanosine, deoxycytidine, and deoxythymidine, the second deoxynucleotide is a deoxynucleotide different from the first deoxynucleotide, and the third deoxynucleotide is a deoxynucleotide complementary to the first deoxynucleotide.

<2> A method for determining a sequence adjacent to a specific sequence in a nucleotide strand, comprising the steps of:

amplifying the adjacent sequence by the method according to <1>; and performing sequence analysis on the amplified adjacent sequence.

<3> The method according to <1> or <2>, wherein the first reverse primer is a primer containing an adapter primer sequence, an oligonucleotide composed of a third deoxynucleotide, a fourth deoxynucleotide, and a fifth deoxynucleotide in order from the 5'-end, the fourth deoxynucleotide is a deoxynucleotide randomly selected from three types other than the third deoxynucleotide, and the fifth deoxynucleotide is a deoxynucleotide randomly selected from the four types.

<4> The method according to any one of <1> to <3>, wherein the specific sequence is a sequence derived from a foreign gene inserted in a DNA strand, and the adjacent sequence is a sequence derived from a host genome adjacent to foreign gene insertion inserted in the DNA strand.

<5> A kit for use in the method according to any one of <1> to <4>, comprising: a first forward primer; a second forward primer; a third forward primer; a first reverse primer; and a second reverse primer.

Advantageous Effects of Invention

According to the present invention, it is possible to amplify a sequence adjacent to a specific sequence in a short time with high efficiency, high sensitivity, low cost, high versatility, and good reproducibility, and to even determine the sequence.

DESCRIPTION OF EMBODIMENTS

Method of the Present Invention

Figure 1:
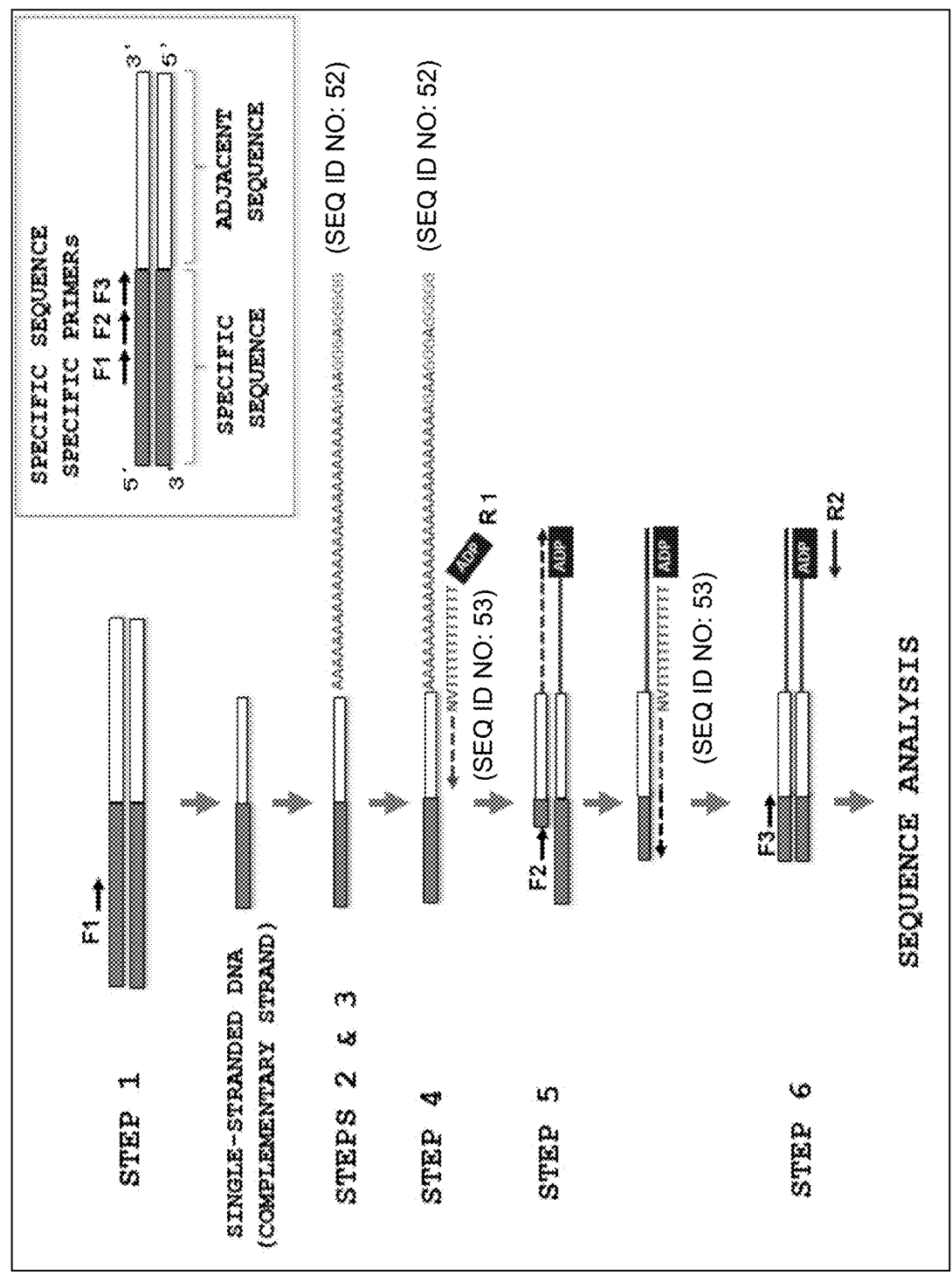
FIG. 1 is a schematic diagram showing an embodiment of a method for amplifying a sequence adjacent to a specific sequence of the present invention and a method for determining the sequence.

The present invention is a method for amplifying a sequence adjacent to a specific sequence in a nucleotide strand, comprising the following steps (1) to (6):

(1) a step of annealing a first forward primer to the specific sequence, performing an extension reaction with the primer as a starting point, and synthesizing a complementary strand containing a sequence complementary to the adjacent sequence at a 3'-end;

(2) a step of polymerically adding a first deoxynucleotide to the 3'-end of the complementary strand obtained in step (1);

(3) a step of further polymerically adding a second deoxynucleotide to a 3'-end of a polydeoxynucleotide strand composed of the first deoxynucleotide added in step (2);

(4) a step of annealing a first reverse primer to a binding site between the 3'-end of the complementary strand and the polydeoxynucleotide strand in a single-stranded DNA formed in step (3), performing an extension reaction with the primer as a starting point, and synthesizing a double-stranded DNA;

(5) a step of performing a polymerase chain reaction with the double-stranded DNA synthesized in step (4) as a template by using a second forward primer complementary to the specific sequence and a first reverse primer; and (6) a step of further performing a polymerase chain reaction with an amplification product obtained in step (5) as a template by using a third forward primer complementary to the specific sequence and a second reverse primer.

Note that the second forward primer is located closer to the adjacent sequence than the first forward primer in the specific sequence, and the third forward primer is located closer to the adjacent sequence than the second forward primer in the specific sequence.

The first reverse primer is a primer containing an adapter primer sequence and an oligonucleotide composed of a third deoxynucleotide in order from a 5'-end, and the second reverse primer is a primer containing an adapter primer sequence at the 3'-end.

The first to third deoxynucleotides are a first deoxynucleotide, each selected from four types consisting of deoxyadenosine, deoxyguanosine, deoxycytidine, and deoxythymidine, the second deoxynucleotide is a deoxynucleotide different from the first deoxynucleotide, and the third deoxynucleotide is a deoxynucleotide complementary to the first deoxynucleotide.

The "nucleotide strand" used in the method of the present invention is not particularly limited as long as it can include a specific sequence described later and a sequence adjacent thereto (adjacent sequence), and example thereof is a polymer of nucleotides isolated from living organisms such as animals and plants (such as tissues and cells), cultured cells, foods, environment (such as soil and wastewater), and the like. Further, the nucleotide strand used in the method of the present invention may be a polymer of deoxynucleotide (DNA strand) or a polymer of ribonucleotide (RNA strand).

The nucleotide strand used in the method of the present invention can be isolated from the living organisms and the like by any method. For example, a method using a dissolution treatment with a surfactant (such as CTAB), a sonic treatment, shaking stirring using glass beads, a French press, or the like can be mentioned. Purification of nucleotide strands can be carried out, for example, by phenol extraction, chromatography, ion exchange, gel electrophoresis, density-dependent centrifugation, and the like. More specifically, the nucleotide strand used in the method of the present invention includes double-stranded nucleic acids such as genomic DNA and PCR fragments isolated by the method described above, and single-stranded nucleic acids such as total RNA or mRNA, or cDNA prepared from such RNA by reverse transcription reaction.

The "specific sequence" is not particularly limited as long as the sequence has already been specified, and examples thereof include foreign DNA (foreign gene) inserted into the genomic DNA (host genome) of a host cell. More specific examples of the foreign gene include transgenes (such as a knock-in gene and vector used for genetic recombination and the like, and a knock-in gene of genome editing (SDN-3)), viral DNAs (such as HTLV-1, HIV, SIV, HBV, HBV, MCV, adenovirus, retrovirus, and lentivirus), and parts thereof. In addition, examples of the "specific sequence" according to the present invention include sequences encoding constant regions in nucleotides encoding antigen-binding polypeptides such as the T-cell receptor (TCR), B-cell receptor (BCR), or antibodies, and parts thereof.

The "adjacent sequence" means a sequence adjacent to at least one of the 5'-side and the 3'-side of the specific sequence. Examples thereof include a sequence derived from a host genome, adjacent to the foreign gene, and a sequence encoding a variable region such as TCR, adjacent to the sequence encoding the constant region.

Hereinafter, preferred embodiments of the present invention will be described in detail with reference to FIG. 1 in the order of the steps, but the present invention is not limited to the aspects shown in FIG. 1.

(Step (1) Synthesis of Complementary Strand)

The step anneals a first forward primer ("F1" in the figure) to the specific sequence, performs an extension reaction from the specific sequence to the adjacent sequence with the primer as a starting point, and synthesizes a single-stranded DNA containing a sequence complementary to the adjacent sequence at the 3'-end.

The "primer" means a polynucleotide molecule that can specifically anneal to a template polynucleotide and provides a 3'-end as a substrate (starting point) for a template-dependent polymerase to produce an extension product that is complementary to the template polynucleotide. The "extension reaction" means the template-dependent integration of at least one complementary nucleotide into the 3'-end of the annealed primer.

"Complementary" means that when two polynucleotides anneal to each other, adenine (A) pairs with thymine (T) or uracil (U), and guanine (G) pairs with cytosine (C), and base pairing selectivity is due to hydrogen bonding between these bases. Furthermore, in the present invention, "complementary" means having at least 80% complementarity (for example, 85% or more complementarity, preferably 90% or more complementarity (91%, 92%, 93%, 94%), more preferably 95% or more complementarity (96%, 97%, 98%, 99%), and particularly preferably 100% complementarity) to the sequence of the polynucleotide of interest over its entire length or part thereof.

The chain length of the complementary strand synthesized in step (1) is not particularly limited as long as it contains a sequence complementary to the adjacent sequence at the 3'-end, and can be the length analyzable by the sequence analysis methods described later. More specifically, in order to be compatible with libraries for next-generation sequence analysis by Illumina, the sequence complementary to the adjacent sequence may be of a chain length long enough to contain preferably 200 to 2000 nucleotides, and more preferably 400 to 1000 nucleotides.

The synthesis of the complementary strand in the step (1) can be carried out, for example, by repeating a cycle of two steps, a step of annealing a first forward primer, complementary to the specific sequence, to a nucleotide strand to perform an extension reaction with DNA polymerase with the primer as a starting point, and a step of dissociating a double strand containing a sequence synthesized by the step by heat denaturation into a single strand. Note that when the nucleotide strand according to the present invention is an RNA strand, an extension reaction (reverse transcription reaction) can be carried out by using an RNA-dependent DNA polymerase as the DNA polymerase.

The temperature in the step of performing the extension reaction is not particularly limited as long as it is a temperature at which the complementary strand can be synthesized, and can be appropriately adjusted by those skilled in the art, but is preferably 50 to 80° C., and more preferably 50 to 70° C. The retention time is not particularly limited, and can be appropriately set by those skilled in the art according to the desired chain length of the complementary strand, the type of DNA polymerase used, and the like, and is, for example, 10 seconds to 20 minutes. Further, the temperature in the extension step may be the same temperature in all the cycles or may be different.

The temperature in the heat denaturation step is not particularly limited as long as it is a temperature at which the double strand can be dissociated, and can be appropriately adjusted by those skilled in the art, but is preferably 80 to 100° C., more preferably 90 to 99° C., and further preferably 94 to 98° C. In addition, the retention time is not particularly limited, but is preferably 1 second to 5 minutes, more preferably 5 seconds to 3 minutes, and further preferably 10 seconds to 2 minutes.

In the complementary strand formation in step (1), the number of cycles is not particularly limited as long as amplification is possible to the extent that a template can be formed in the step described later, and can be appropriately adjusted by those skilled in the art according to the type and the like of DNA polymerase used, but is preferably 10 to 50 cycles, more preferably 15 to 40 cycles, and further preferably 20 to 30 cycles.

The composition of the reaction solution in such complementary strand synthesis is not particularly limited as long as it contains essential components for performing the synthesis. Examples of components contained in the reaction solution include, in addition to the first forward primer described later and the DNA polymerase described later, substrates such as deoxynucleotides (dNTP), divalent ions (such as magnesium ions and calcium ions) and monovalent ions (such as sodium ions and potassium ions), or salts to provide them (such as magnesium sulfate, magnesium acetate, and magnesium chloride), and buffer solutions (such as Tris hydrochloric acid buffer, phosphate buffer, and HEPES buffer). Also, in addition to these, the reaction solution may contain, as additives, solvents (such as ethanol, methanol, acetone, and dimethyl sulfoxide), organic acids (such as formic acid, acetic acid, and benzoic acid), surfactants (such as SDS and Triton X-100), amino acids (such as aspartic acid, glutamic acid, lysine, and tryptophan), proteins (such as BSA and DNA binding protein), sugars (such as glucose, xylose, and galactose), reducing agents (such as DTT), and betaine. Further, when the nucleotide strand according to the present invention is an RNA strand, a ribonuclease (RNase) inhibitor may be contained in order to suppress the degradation of RNA, and moreover, in order to suppress a decrease in the efficiency of reverse transcription reaction, a reverse transcription reaction auxiliary reagent (such as trade name: RTmate manufactured by Nippon Gene Co., Ltd. (RNA composed of 976 nucleotides synthesized with T7 RNA polymerase)) may be contained.

Further, the complementary strand thus synthesized may be subjected to a purification treatment before being subjected to the following step (2). The purification treatment is not particularly limited as long as the first primer or the like can be removed, and those skilled in the art can appropriately use a known method. Known methods include phenol/chloroform treatment, precipitation treatment with isopropanol or ethanol, and purification using a column. Examples of the column include a DNA adsorption column (as a carrier of the column, silica gel, glass, or the like), a gel filtration column, an anion exchanger, and an ultrafiltration column. A commercially available product is also preferably used for such a column. Examples of commercially available columns for purifying complementary strands (single-stranded DNA) include Monarch PCR & DNA Cleanup Kit (manufactured by New England Biolabs), ssDNA/RNA Clean & Concentrator (manufactured by ZYMO RESEARCH), and Elutip-d DNA purification minicolumns (manufactured by GE healthcare).

(Step (2) Polymeric Addition of First Deoxynucleotide to 3'-End of Complementary Strand)

The step polymerically adds a first deoxynucleotide to the 3'-end of the complementary strand isolated in step (1).

The first deoxynucleotide polymerized in step (2) is not particularly limited as long as it is any one of four types consisting of deoxyadenosine, deoxyguanosine, deoxycytidine, and deoxythymidine, and it is preferably deoxyadenosine, deoxycytidine, or deoxythymidine, and more preferably deoxyadenosine, from the viewpoint that the polymeric addition reaction is more likely to proceed and the chain length of the polydeoxynucleotide strand formed per unit time is likely to be long, and from the viewpoint that the annealing temperature of the polydeoxynucleotide strand and the first reverse primer ("R1" in FIG. 1) described later can be suppressed to a relatively low level.

Further, the chain length of the polydeoxynucleotide strand composed of the first deoxynucleotide polymerically added to the 3'-end of the complementary strand (hereinafter also referred to as the "first polydeoxynucleotide strand") is not particularly limited, and it is preferably 20 to 300 nucleotides from the viewpoint that the first reverse primer ("R1" in FIG. 1) described later can be more specifically annealed to the binding site between the polydeoxynucleotide strand and the 3'-end of the complementary strand.

The polymeric addition of the first deoxynucleotide to the 3'-end of the complementary strand can be performed, for example, by using terminal deoxytransferase to utilize its activity in catalyzing the deoxynucleotide polymerization reaction to the 3' OH end of the DNA.

The temperature of such an enzymatic reaction is not particularly limited, and is usually 30 to 40° C., and preferably 37° C. In addition, the reaction time can be appropriately set by those skilled in the art according to the desired chain length of the complementary strand, but is preferably 5 to 40 minutes, and more preferably 10 to 30 minutes.

The composition of the reaction solution in such a polymeric addition is not particularly limited as long as it contains compositions essential for carrying out the addition. Examples of compositions contained in the reaction solution include, in addition to the first deoxynucleotide and terminal deoxytransferase, divalent ions (such as manganese ions, cobalt ions, and magnesium ions) or salts to provide them (such as manganese chloride, cobalt chloride, and magnesium chloride), and buffer solutions (such as HEPES buffer, Tris hydrochloric acid buffer, and phosphate buffer). Also, in addition to these, the reaction solution may contain, as additives, reducing agents (such as DTT), proteins (such as BSA and DNA binding protein), solvents (such as ethanol, methanol, acetone, and dimethyl sulfoxide), organic acids (such as formic acid, acetic acid, and benzoic acid), surfactants (such as SDS and Triton X-100), amino acids (such as aspartic acid, glutamic acid, lysine, and tryptophan), sugars (such as glucose, xylose, and galactose), and betaine.

(Step (3) Polymeric Addition of Second Deoxynucleotide to 3'-End of First Polydeoxynucleotide Strand)

The step further polymerically adds a second deoxynucleotide to a 3'-end of the first polydeoxynucleotide strand added in step (2).

The second deoxynucleotide polymerized in step (3) is any of four types consisting of deoxyadenosine, deoxyguanosine, deoxycytidine, and deoxythymidine, and is a deoxynucleotide different from the first deoxynucleotide, but is preferably deoxyguanosine from the viewpoint that the polymeric addition reaction is difficult to proceed and the chain length of the polydeoxynucleotide strand formed per unit time can be easily adjusted.

The chain length of the polydeoxynucleotide strand composed of the second deoxynucleotide added to the 3'-end of the first polydeoxynucleotide strand (hereinafter also referred to as the "second polydeoxynucleotide strand") is not particularly limited as long as it can suppress non-specific synthesis by the first reverse primer ("R1" in FIG. 1) described later, but is preferably 1 to 300 nucleotides. Further, the second polydeoxynucleotide strand may contain deoxynucleotides other than the second deoxynucleotide. The other deoxynucleotides are not particularly limited, and examples thereof include deoxynucleotides of the same type as the first deoxynucleotide.

The polymeric addition of the second deoxynucleotide to the 3'-end of the first polydeoxynucleotide strand can be performed, for example, by using the enzymatic reaction of terminal deoxytransferase, as in the case of the first deoxynucleotide.

The temperature of such an enzymatic reaction is not particularly limited, and is usually 30 to 40° C., and preferably 37° C. In addition, the reaction time can be appropriately set by those skilled in the art according to the desired chain length of the complementary strand, but is preferably 2 to 40 minutes, more preferably 5 to 30 minutes, and further preferably 10 to 20 minutes.

Further, the reaction solution in such a polymeric addition can be prepared by adding a second deoxynucleotide to the reaction solution in step (2) above.

Then, the single-stranded DNA added with the second polydeoxynucleotide strand via the first polydeoxynucleotide strand at the 3'-end of the complementary strand may be subjected to heat treatment to deactivate the enzymatic activity of terminal deoxytransferase. The conditions of such heat treatment are not particularly limited as long as the enzyme is deactivated, but the enzyme can be usually deactivated by incubation at 60 to 90° C. (preferably 70 to 80° C.) for 1 minute to 1 hour (preferably 5 to 20 minutes).

(Step (4) Synthesis of Double-Stranded DNA)

The step anneals a first reverse primer ("R1" in FIG. 1) to a binding site between the 3'-end of the complementary strand and the first polydeoxynucleotide strand in a single-stranded DNA formed in step (3), performing an extension reaction with the primer as a starting point, and synthesizing a double-stranded DNA.

In step (4), the double-stranded DNA can be synthesized, for example, by annealing the first reverse primer to the single-stranded DNA after heat denaturation treatment, and using the primer as a starting point for the extension reaction with DNA polymerase.

The enzyme used in the step is not particularly limited as long as the extension reaction can be carried out, but is preferably a DNA polymerase that exhibits its activity even in the presence of cobalt chloride. Cobalt chloride is a salt normally added to a polymeric addition reaction system with terminal deoxytransferase as described above, and therefore, the use of a DNA polymerase capable of an extension reaction even in the presence of the salt makes it possible to carry out steps (2) to (5) above in one pot without requiring purification treatment or the like. Examples of such DNA polymerase include Q5 DNA Polymerase (such as Q5 High-Fidelity DNA Polymerase and Q5 Hot Start High-Fidelity DNA Polymerase, both manufactured by New England Biolabs).

The temperature in the heat denaturation step is not particularly limited as long as it can denature the higher-order structure of the single-stranded DNA, but is preferably 30 to 100° C., and more preferably 50 to 99° C. The retention time is not particularly limited, and is, for example, 1 second to 10 minutes.

The temperature in the annealing step is not particularly limited as long as it is a temperature at which annealing of the first reverse primer and the single-stranded DNA can occur and be maintained, but is preferably 40 to 80° C., more preferably 45 to 70° C., and further preferably 50 to 65° C., from the viewpoint of suppressing non-specific amplification products. The retention time is not particularly limited, but is preferably 30 seconds to 5 minutes, and more preferably 1 to 2 minutes. Further, the annealing temperature may be the same temperature or may be different. For example, a temperature gradient of a few degrees Celsius (2 to 3° C.) every 10 seconds will make it easier for the first reverse primer to specifically anneal to its 3'-end such that it glides down the first polydeoxynucleotide strand.

The temperature in the extension step is not particularly limited as long as it is a temperature at which double strands can be synthesized, and can be appropriately adjusted by those skilled in the art, but is preferably 50 to 80° C., more preferably 65 to 75° C., and particularly preferably 72° C. In addition, the retention time is not particularly limited, but is preferably 10 seconds to 5 minutes, more preferably 30 seconds to 2 minutes, and particularly preferably 1 minute. Note that the annealing temperature may be the same as the temperature in the extension step, but is not set higher than the temperature in the extension step.

Note that the above reaction can be carried out by using the same reaction solution as in step (1). In addition, after the extension reaction, the enzyme activity of DNA polymerase is suppressed and the double-stranded DNA structure is maintained, so that the temperature is usually maintained at 4° C.

(Step (5) First Polymerase Chain Reaction)

The step performs a polymerase chain reaction with the double-stranded DNA synthesized in step (4) as a template by using a second forward primer complementary to the specific sequence ("F2" in FIG. 1) and a first reverse primer ("R1" in FIG. 1).

The "polymerase chain reaction (PCR)" means amplifying a target nucleotide sequence by repeating temperature changes. More specifically, PCR includes a cycle composed of the following three steps, a step for annealing a forward primer and a reverse primer to a target nucleotide sequence, then a step of using the primer as a starting point for the extension reaction with DNA polymerase, and a step of dissociating a double strand containing a target nucleotide sequence synthesized by the step by heat denaturation into a single strand.

The annealing temperature in step (5) is not particularly limited as long as the annealing can occur and be maintained, and can be appropriately adjusted by those skilled in the art, but is preferably 50 to 80° C., and more preferably 60 to 70° C., from the viewpoint of suppressing non-specific amplification products. Further, the retention time is not particularly limited, but is preferably 1 to 60 seconds. Note that the annealing temperature may be the same or different in all the cycles.

The temperature in the step of performing the extension reaction is not particularly limited as long as it is a temperature at which the complementary strand can be synthesized, but is preferably 50 to 80° C., more preferably 65 to 75° C., and particularly preferably 72° C. The retention time is not particularly limited, but is preferably 1 to 60 seconds, more preferably 10 to 50 seconds, further preferably 20 to 40 seconds, and particularly preferably 30 seconds. Further, the temperature in the step of performing the extension reaction may be the same temperature or different in all the cycles. The annealing temperature may be the same as the temperature in the step of performing the extension reaction, but is not set higher than the temperature in the extension step.

The temperature in the heat denaturation step is not particularly limited as long as it is a temperature at which the double strand can be dissociated, but is preferably 80 to 100° C., more preferably 95 to 99° C., and particularly preferably 98° C. The retention time is not particularly limited, but is preferably 1 to 60 seconds, more preferably 10 to 50 seconds, further preferably 20 to 40 seconds, and particularly preferably 30 seconds.

In the PCR in step (5), the number of cycles is not particularly limited as long as amplification is possible to the extent that a template can be formed in the step described later, but is preferably 10 to 40 cycles, more preferably 15 to 30 cycles, and even more preferably 20 to 25 cycles.

Note that the above PCR can be carried out by using the same reaction solution as in step (1) (step (4)). That is, the PCR in step (5) can be carried out by adding an F2 primer after the reaction in step (4) and repeating the above temperature changes.

The amplification product thus obtained may be subjected to a purification treatment before being subjected to the following step (6). The purification treatment is the same as the purification treatment described in step (1). Further, as the purification column, a commercially available product is also preferably used, and examples of commercially available columns for purifying such PCR amplification products include Ampure XP (manufactured by Beckman Coulter) and GenElute PCR Clean-Up Kit (manufactured by Merck).

Further, in the following step (6), the amplification product may be diluted and used as a template without performing the purification treatment. The dilution ratio is not particularly limited and can be appropriately adjusted by those skilled in the art, but is usually 10 to 1000 times, preferably 100 to 500 times, and more preferably 200 to 300 times.

(Step (6) Second Polymerase Chain Reaction)

The step performs a PCR with an amplification product synthesized in step (5) as a template by using a third forward primer ("F3" in FIG. 1) complementary to the specific sequence and a second reverse primer ("R2" in FIG. 1).

The PCR is as described above, but the conditions can be the same, for example, in the annealing and extension reactions in step (6). The temperature is not particularly limited as long as the amplification product synthesized in step (5) is annealed with the third forward primer or the second reverse primer and the complementary strand can be synthesized, and can be appropriately adjusted by those skilled in the art, but is preferably 50 to 80° C., and more preferably 60 to 70° C., from the viewpoint of suppressing non-specific amplification products. The retention time is not particularly limited, but is preferably 5 seconds to 2 minutes, more preferably 10 seconds to 1 minute, further preferably 20 to 40 seconds, and particularly preferably 30 seconds. Note that the temperature in the annealing and extension reactions may be different, but is not set higher than the temperature in the extension step. Further, the annealing temperature and/or the temperature in the extension reaction may be the same temperature or different in all the cycles.

The temperature in the heat denaturation step is not particularly limited as long as it is a temperature at which the double strand can be dissociated, and can be appropriately adjusted by those skilled in the art, but is preferably 80 to 100° C., more preferably 90 to 99° C., and further preferably 94 to 98° C. The retention time is not particularly limited, but is preferably 1 second to 5 minutes, more preferably 5 seconds to 3 minutes, and further preferably 10 seconds to 2 minutes.

In the PCR in step (6), the number of cycles is not particularly limited as long as amplification is possible to the extent that detection is possible or to the extent that sequence analysis is possible by the method described later, but is preferably 10 to 50 cycles, more preferably 25 to 40 cycles, and further preferably 30 to 35 cycles.

Note that the above PCR can also be carried out by using the same reaction solution as in step (1) in the same manner as in step (4) and step (5).

Then, by going through the above steps, according to the present invention, the adjacent sequence can be amplified as shown in FIG. 1. Note that as shown in the figure, not only the adjacent sequence but also a part of the specific sequence and a part of the first polydeoxynucleotide strand are amplified together. Further, in PCR, the relationship between the template polynucleotide and the complementary strand having a sequence complementary thereto is merely relative. That is, the strand synthesized as a complementary strand can function as a template again. Therefore, the adjacent sequence and the like that are the targets of amplification or sequencing described later in the present invention include not only the sequence but also a complementary strand of the sequence.

Those skilled in the art can detect or confirm the amplified adjacent sequence or the like in the present invention by appropriately using a known method. Known methods include electrophoresis (such as electrophoresis that develops an amplification product on an agarose gel or acrylamide gel), nucleic acid chromatography, intercalation, quencher-mediated fluorescence detection, and Southern blotting.
(Sequence Analysis)

By determining the sequence of the amplification product obtained through the above steps, the adjacent sequence can be clarified. Such sequencing can be performed by known sequence analysis. For example, the amplification product can be isolated, subcloned into a vector, and sequenced using Sanger sequencing or dye terminator sequencing. In addition, by subjecting to next-generation sequencing (NGS) or single-molecule sequencing, sequencing is possible without the need for a subcloning step.

The next-generation sequencing is not particularly limited, and examples thereof include sequencing-by-synthesis (for example, sequencing with Solexa Genome Analyzer, Hiseq (registered trademark), Nextseq, Miseq, or Miniseq, manufactured by Illumina), pyrosequencing (for example, sequencing with a sequencer GSLX or FLX, manufactured by Roche Diagnostics (454) (so-called 454 sequencing)), and ligase reaction sequencing (for example, sequencing with SoliD (registered trademark) or 5500xl, manufactured by Life Technologies). Examples of single-molecule sequencing include PacBio RS II or PacBio Sequel Systems manufactured by Pacific Biosciences of California, and PromethION, GridION, or MinION manufactured by Oxford Nanopore Technologies.

Further, by determining the adjacent sequence in this way, for example, by further subjecting the sequence to a BLAST search, it is possible to determine the position of the host genome inserted with the foreign DNA which is a specific sequence.

Kit of the Present Invention

As described above, according to the present invention, by carrying out each reaction using the above-mentioned primers, it is possible to amplify the sequence adjacent to a specific sequence and further determine the sequence. Therefore, the present invention provides a kit for use in the method, comprising: a first forward primer; a second forward primer; a third forward primer; a first reverse primer; and a second reverse primer.

As described above, the first forward primer, the second forward primer, and the third forward primer are each a primer having a sequence complementary to the specific sequence, and as shown in FIG. 1, the second forward primer is located closer to the adjacent sequence than the first forward primer, and the third forward primer is located closer to the adjacent sequence than the second forward primer. Note that "closer to the adjacent sequence" may mean that the annealing position at the 5'-end of the primer is closer to the adjacent sequence, and the annealing regions of the forward primer may partially overlap. The annealing position is not particularly limited, and can be appropriately adjusted by those skilled in the art based on the specific sequence information, and the annealing positions of the first to third forward primers (annealing positions at the 5'-ends of the primers) are each preferably 1000 to 200 nucleotides, 500 to 80 nucleotides, and 300 to 30 nucleotides, from the boundary between the specific sequence and the adjacent sequence.

In addition, when the specific sequence is a sequence derived from a foreign DNA having an LTR, it is desirable that the first forward primer be annealed outside the LTR regions, from the viewpoint that if the first forward primer is annealed in an LTR region, the virus-derived DNA sandwiched between the LTR regions (5'-LTR and 3'-LTR) may also be amplified.

The chain length of the first to third forward primers is not particularly limited, but the length of the sequence portion complementary to the specific sequence is preferably 18 to 27 nucleotides, and more preferably 18 to 25 nucleotides.

The melting temperature (Tm) value of the first to third forward primers is preferably 57 to 72° C., more preferably 62 to 70° C., and particularly preferably 68° C.

Note that a primer having such a desired chain length and Tm value can be designed by those skilled in the art by using a PCR primer design tool. Examples of such a design tool include Primer3.

The first reverse primer is a primer containing at least an adapter primer sequence and an oligonucleotide composed of a third deoxynucleotide in order from a 5'-end. As described above, the primer must have an oligonucleotide composed of a third deoxynucleotide, which is a deoxynucleotide complementary to the first deoxynucleotide, in order to anneal to the binding site between the 3'-end of the above complementary strand and the first polydeoxynucleotide strand. Further, as shown in Examples described later, from the viewpoint that the binding site between the sequence complementary to the adjacent sequence and the first polydeoxynucleotide strand facilitates highly specific annealing, the first reverse primer is preferably a primer further containing a fourth deoxynucleotide at the 3'-end (that is, a primer containing an adapter primer sequence, an oligonucleotide composed of a third deoxynucleotide, and a fourth deoxynucleotide in order from the 5'-end), and more preferably a primer containing a fourth deoxynucleotide and a fifth deoxynucleotide on the 3'-side (that is, a primer containing an adapter primer sequence, an oligonucleotide composed of a third deoxynucleotide, a fourth deoxynucleotide, and a fifth deoxynucleotide in order from the 5'-end).

Note that the fourth deoxynucleotide is a deoxynucleotide randomly selected from three types other than the third deoxynucleotide, and the fifth deoxynucleotide is a deoxynucleotide randomly selected from four types. Specifically, the first to fifth deoxynucleotides have the relationships shown in Table 1 below.

TABLE 1

| First | Second | Third | Fourth | Fifth |
|-------|--------|-------|--------|-------|
| dA | dG, dC, or dT | dT | Other than dT (dV) | Any (dN) |
| dG | dA, dC, or dT | dC | Other than dC (dD) | |
| dC | dA, dG, or dT | dG | Other than dG (dH) | |
| dT | dA, dG, or dC | dA | Other than dA (dB) | |

The chain length of the oligonucleotide composed of a third deoxynucleotide is not particularly limited as long as it can sufficiently anneal to the first polydeoxynucleotide strand, and can be appropriately adjusted by those skilled in the art according to the type of deoxynucleotide to be contained, but is preferably 5 to 30 nucleotides, and more preferably 10 to 25 nucleotides. Note that the fourth deoxynucleotide and the fifth nucleotide are contained in the first reverse primer by one nucleotide each.

The first reverse primer further contains an adapter primer sequence on the 5'-side. In addition, the second reverse primer also contains an adapter primer sequence at the 3'-end. It is preferable that in the present invention, the "adapter primer sequence" is not at least a sequence complementary to the specific sequence, the first polydeoxynucleotide strand, and the second polydeoxynucleotide strand according to the present invention, and is furthermore not a sequence complementary to the DNA strand according to the present invention (for example, a host genome inserted with a foreign DNA). Further, it is more preferable that the adapter primer sequence is a sequence that does not exist in nature.

The chain length of the adapter primer sequence is not particularly limited as long as the above-mentioned second polymerase chain reaction (step (6)) can sufficiently proceed, and can be appropriately adjusted by those skilled in the art, but is preferably 18 to 27 nucleotides, more preferably 20 to 25 nucleotides, and particularly preferably 22 nucleotides. The melting temperature (Tm) value of the adapter primer sequence is preferably 50 to 72° C., and more preferably 55 to 68° C.

Preferred examples of adapter primer sequences are shown in Table 2 below.

TABLE 2

| Sequence Name | Sequence (5'→3') | SEQ ID NO: |
|---------------|------------------|------------|
| ADP1 | ACACAGGTCATCAAGCAGTA | 2 |
| ADP2 | AGCAGTAGCAGCAGTTCGATAA | 3 |
| M13-20 | GTAAAACGACGGCCAGT | 4 |
| M13-21 | TGTAAAACGACGGCCAGT | 5 |
| M13-47 | CGCCAGGGTTTTCCCAGTCACGAC | 6 |
| M13-P5 | CAGGAAACAGCTATGAC | 7 |
| M13rev | GAGCGGATAACAATTTCACACAGG | 8 |
| T3 | ATTAACCCTCACTAAAGGGAA | 9 |
| T3pro | ATTAACCCTCACTAAAGGGA | 10 |

TABLE 2-continued

| Sequence Name | Sequence (5'→3') | SEQ ID NO: |
|---------------|------------------|------------|
| T7 | TAATACGACTCACTATAGGG | 11 |
| T7term | GCTAGTTATTGCTCAGCGG | 12 |
| BGHrev | TAGAAGGCACAGTCGAGG | 13 |
| SP6 | CATACGAPTTAGGTGACACTATAG | 14 |
| SP6-II | ATTTAGGTGACACTATAGAATA | 15 |
| SP6pro | GATTEAGGTGACACTATAG | 16 |

In the present invention, the "nucleotide" constituting a primer is usually a DNA, but may be another natural nucleotide (RNA) or may include an unnatural nucleotide (artificial nucleotide, nucleotide analog) as long as it can form a base pair bond. Examples of unnatural nucleotides include hexitol nucleic acids (HNA), cyclohexene nucleic acids (CeNA), peptide nucleic acids (PNA), glycol nucleic acids (GNA), threose nucleic acids (TNA), morpholino nucleic acids, tricyclo-DNA (tcDNA), 2'-O-methylated nucleic acids, 2'-MOE (2'-O-methoxyethyl) nucleic acids, 2'-AP (2'-O-aminopropyl) nucleic acids, 2'-fluorinated nucleic acids, 2'F-arabinose nucleic acids (2'-F-ANA), and BNA (bridged nucleic acids such as LNA).

The "primer" of the present invention is an oligonucleotide that anneals to a target nucleotide sequence and serves as a starting point for DNA replication, and may be an oligonucleotide composed of only one type of nucleotide (for example, DNA only) or a chimeric oligonucleotide composed of more than one type of nucleotides (for example, DNA and RNA), but is preferably an oligonucleotide composed only of DNA.

The primers of the present invention can be prepared by those skilled in the art by appropriately selecting a known method. For example, primers can be prepared by synthesis using a commercially available automated nucleic acid synthesizer (manufactured by Applied Biosystems, Beckman, or the like) and subsequent purification of the resulting oligonucleotide using a reversed-phase column or the like.

In addition, a labeling substance may be bound to the primer of the present invention in order to facilitate detection of an amplification product by PCR. The "labeling substance" is not particularly limited as long as it can bind to a nucleotide and can be detected by a chemical or optical method, and examples thereof include fluorescent proteins such as green fluorescent protein (GFP), allophycocyanin (APC), and phycoerythrin (R-PE), enzymes such as alkaline phosphatase (ALP), horseradish peroxidase (HRP), and β-galactosidase (β-gal), radioisotopes such as $^{125}$I, fluorescent dyes such as fluorescein isothiocyanate (FITC) and rhodamine isothiocyanate (RITC), chromogenic labeling substances such as colloidal metals and colored latex, avidin, biotin, DIG, and anti-DIG antibodies. Note that when an enzyme is used as a labeling substance, various detections are possible depending on the substrate by adding a color-developing substrate, a fluorescent substrate, a chemiluminescent substrate, or the like as the substrate. Further, the binding of the labeling substance may be directly bound to the nucleotide constituting the primer, or may be indirectly bound via another substance.

Further, a sequence for determining the adjacent sequence (for example, an adapter sequence for next-generation sequencer such as flow cell binding region) may be added to the third forward primer and the second reverse primer, as shown in Examples described later.

In addition to the above primers, the kit of the present invention may contain various enzymes used in the reaction. Examples of the enzymes include the above-mentioned DNA polymerase and terminal deoxytransferase (terminal deoxynucleotidyl transferase).

The "DNA polymerase" may be any as long as it has an activity of synthesizing a complementary strand composed of DNA with respect to the target nucleotide sequence (DNA-dependent DNA polymerase, RNA-dependent DNA polymerase), and can be used even when it has normal temperature, medium temperature, and heat resistance. In addition, examples include DNA polymerase having at least one of 5' 4 3' exonuclease activity, 3' 4 5' exonuclease activity (calibration activity), and TdT activity.

The "DNA-dependent DNA polymerase" according to the present invention is not particularly limited, but is preferably a thermostable DNA polymerase. The thermostable DNA polymerase is not particularly limited, and examples thereof include KOD Polymerase (such as KOD-Plus-Neo manufactured by Toyobo Co., Ltd.), Q5 DNA Polymerase (such as Q5 High-Fidelity DNA Polymerase and Q5 Hot Start High-Fidelity DNA Polymerase, both manufactured by New England Biolabs), and Ex Taq Polymerase (manufactured by Takara Bio Inc.).

The "RNA-dependent DNA polymerase" according to the present invention is not particularly limited, and examples thereof include retrovirus-derived reverse transcriptases. More specific examples include mutant Moloney murine leukemia virus (MMLV) reverse transcriptase, avian myeloblastosis virus (AMV) reverse transcriptase, Rous-associated virus (RAV) reverse transcriptase, human immunodeficiency virus (HIV) reverse transcriptase, or variants thereof (for example, SuperScript (registered trademark) reverse transcriptase (manufactured by Thermo Fisher Scientific), which is a mutant of MMLV reverse transcriptase).

The kit of the present invention may further contain a substance necessary for the above reaction. Examples of such substances include the compositions of the above reaction solution (substrate (dNTP), the ions or salts for providing them, buffer solution, and additives). In addition, when a labeling substance is bound to the primer of the present invention, a substrate for detecting the labeling substance may also be included in the kit. Further, depending on the detection method, the kit also appropriately includes a carrier (for example, gel in electrophoresis, chromatographic test paper in nucleic acid chromatography) and solvent for developing the amplification product by PCR, a fluorescent substance (for example, an intercalator in intercalation), and a probe bound with the fluorescent substance and the quencher in the quencher-mediated fluorescence detection. Moreover, DNA molecular weight markers and positive controls for identifying amplified sequences may also be included in the kit. In addition, a substance necessary for sequencing, for example, a primer for sequencing or the like can be included. Furthermore, the kit of the present invention includes an instruction manual for use thereof.

EXAMPLES

Hereinafter, the present invention will be described in more detail based on Examples, but the present invention is not limited to the following Examples.

18

(Preparation of Genomic DNA)

Genomic DNA containing a specific sequence (transgene such as DNA derived from HTLV-1) and a sequence adjacent thereto (sequence derived from the host genome) was isolated and prepared by using QIAamp DNA Blood Mini Kit from manufactured by QIAGEN in accordance with the method described in the attached instruction manual when the samples were peripheral blood leukocytes or cell lines, and by using an alkaline solution by the conventional method when the sample was adenovirus, rat tissue, or corn Bt176 species (http://bch.cbd.int/database/attachment/?id=10723).

Then, as shown in Table 3 below, RNaseA (manufactured by Takara Bio Inc. or Nippon Gene Co., Ltd.) was added to the obtained genomic DNA, which was incubated at 37° C. for 10 minutes to deactivate and remove RNA.

TABLE 3

| Reaction Component | Amount |
|---|---|
| DNA (200 ng/µL) | 2.5 µL |
| RNase A (100 ng/µL) | 0.5 µL |
| Total | 3 µL |

Then, in the step shown in FIG. 1, an attempt was made to amplify a sequence adjacent to the specific sequence.

(Step 1) Synthesis of Complementary Strand

For the synthesis of single-stranded DNA containing a transgene and the host genome, the genomic DNA was used as a template, the transgene-specific F1 primer and the KOD-Plus Neo reaction solution (manufactured by Toyobo Co., Ltd.) were mixed so as to have the composition shown in Table 4 below, and Veriti Thermal Cycler manufactured by Thermo Fisher Scientific was used to carry out the reaction under the conditions shown in Table 5 below (required time: about 40 minutes).

TABLE 4

| Reaction Component | Amount |
|---|---|
| DNA (200 ng/µL) | 3 µL |
| 10× PCR Buffer for KOD-Plus-Neo | 8 µL |
| 2 mM dNTPS | 5 µL |
| 25 mM MgSO$_4$ | 3 µL |
| 10 µM F1 Primer | 1.5 µL |
| KOD-Plus-Neo (1 U/µL) | 1 µL |
| H$_2$O | 31.5 µL |
| Total | 50 µl |

TABLE 5

| PCR Condition | Temperature | Time | Cycle Count |
|---|---|---|---|
| Pre-Cycle Heat Denaturation | 94° C. | 2 Min | 1 |
| Heat Denaturation | 98° C. | 10 Sec | 25 |
| Extension | 68° C. | 30 Sec or 45 Sec* | |

*When the foreign DNA had LTRs, the extension time was set to 45 seconds.

Note that the sequences of each F1 primer, each F2 primer, and each F3 primer described later are as follows. Further, in Table 6 below, "Common" indicates that the primer is commonly used regardless of the type of transgene.

"NNNNNNNN" in the "NGS-F2" sequence indicates an index tag (dual index sequence) used in the Illumina next-generation sequencer described later.

TABLE 6

| Trans-gene | Forward Primer Name | Forward Primer Sequence (5'→3') | SEQ ID NO: |
|---|---|---|---|
| HTLV-1 | HTLV-F1 | CAAGGCCTACCACCCCTCAT | 17 |
| | HTLV-F2 | CCTGACCCTGCTTGCTCAAC | 18 |
| | HTLV-F3 | [Illumina Read 1 Primer Region]-GCCAGCGACAGCCCATTCTAT | 19 |
| HIV-1 | HIV-F1 | CCTGGCTGGAAGCACAAGAGGAG | 20 |
| | HIV-F2 | GGGACTTTCCAGGGAGGTGTGG | 21 |
| | HIV-F3 | [Illumina Read 1 Primer Region]-GCCCGTCTGTTGTGTGACTCTGG | 22 |
| SIV-1 | SIV-F1 | TCAGTGAGGCCAAAAGTTCCCCTA | 23 |
| | SIV-F2 | GAGCCTGGGTGTTCCCTGCTAGA | 24 |
| | SIV-F3 | [Illumina Read 1 Primer Region]-CGCCTGGTCAACTCGGTACTCAA | 25 |
| HBV-1 | HBV-F1 | GCCAGGTCTGTGGCAAGTGTTTG | 26 |
| | HBV-F2 | TCTGTGCCAAGTGTTTGCTGACG | 27 |
| | HBV-F3 | [Illumina Read 1 Primer Region]-CACTGGCTGGGGCTTGGTCAT | 28 |
| ADV-1 | ADV-F1 | CTGAAATGTGTGGGCGTGGCTTA | 29 |
| | ADV-F2 | CTGCGGGGTGGTGTTGTAGATGA | 30 |
| | ADV-F3 | [Illumina Read 1 Primer Region]-CTGGGCGTGGTGCCTAAAAATGT | 31 |
| Idlr- | Idlr-LoxP-F1 | GAAAGGGGGTTTGAATGGTGTGG | 32 |
| LoxP | Idlr-LoxP-F2 | TGAGGGGTGGTCTAGCCTGATGG | 33 |
| | Idlr-LoxP-F3 | [Illumina Read 1 Primer Region]-TGGGCACACTGAAGAGGACAAATG | 34 |
| Btl76 | Btl76-F1 | CTTCACCACCCCCTTCAACTTC | 35 |
| | Btl76-F2 | AGTACGACCTGGAGAGGGCTCA | 36 |
| | Btl76-F3 | [Illumina Read 1 Primer Region]-AAGACCGACGTGACCGACTACC | 37 |
| Common | Banger seq primer | ACACTCTTTCCCTACACGAC | 38 |
| | NGS-F2 | AATGATACGGCGACCACCGAGATCTACACNNN NNNNNACACTCTTTCCCTACACGACGC | 39 |

Illumina Read 1 Primer Region - ACACTCTTTCCCTACACGACGCTCTTCCGATCT (SEQ ID NO: 40)

Purification of the synthesized single-stranded DNA and removal of the F1 primer were carried out using Monarch PCR & DNA Cleanup Kit (manufactured by New England Biolabs, product number: T1030). The single-stranded DNA once bound to the column attached to the kit was eluted by adding 9.2 μL of water, and as a result, 8.2 μL of the sample was collected (required time: about 15 minutes).

(Steps 2 and 3) Poly-AG Tailing at 3'-End of the Complementary Strand

PolyA tailing of the 3'-end of the single-stranded DNA described above was performed by mixing the purified single-stranded DNA, terminal deoxytransferase (TdT) reaction solution (manufactured by New England Biolabs), and dATP to the composition shown in Table 7 below and reacting at 37° C. for 20 minutes.

TABLE 7

| Reaction Component | Amount |
|---|---|
| Single-Stranded DNA | 8.2 µL |
| 10X TdT Buffer | 1.1 µL |
| 2.5 mM CoCl₂ | 1.1 µL |
| 10 mM dATP | 0.35 µL |
| TdT | 0.25 µL |
| Total | 11 µL |

Then, dGTP was added so as to have the composition shown in Table 8 below, which was further reacted at 37° C. for 15 minutes to add poly AG to the 3'-end of the single-stranded DNA.

TABLE 8

| Reaction Component | Amount |
|---|---|
| Single-Stranded DNA | 11 µL |
| 10X TdT Buffer | 0.1 µL |
| 2.5 mM CoCl₂ | 0.1 µL |
| 1.0 mM dGTP | 0.35 µL |
| H₂O | 0.45 µL |
| Total | 12 µL |

Then, the terminal deoxytransferase was inactivated by heat treatment at 75° C. for 10 minutes (required time: about 45 minutes).

(Step 4) Synthesis of Double-Stranded DNA

For the synthesis of double-stranded DNA, oligo dT adapter primers (SEQ ID NOs: 2 and 41) and Q5 Hot Start High-Fidelity DNA Polymerase reaction solution (manufactured by New England Biolabs) were added directly to the reaction solution of step 3 described above so as to have the composition shown in Table 9 below, and Veriti Thermal Cycler manufactured by Thermo Fisher Scientific was used to carry out the reaction under the touchdown conditions shown in Table 10 below (required time: about 5 minutes). Note that the obtained sample was maintained at 4° C. until the next step was started.

TABLE 9

| Reaction Component | Amount |
|---|---|
| Single-Stranded DNA | 12 µL |
| 5× Q5 Reaction surfer | 12 µL |
| 10 mM dNTPS | 1.2 µL |
| 10 µM Oligo-dT (23) Adapter | 3 µL |
| Q5 HS-High-Fidelity DNA Polymerase | 0.6 µL |
| H₂O | 31.2 µL |
| Total | 60 µL |

TABLE 10

| PCR Condition | Temperature | Time | Cycle |
|---|---|---|---|
| Heat Denaturation | 98° C. | 30 Sec | 1 |
| Annealing | 64° C. | 10 Sec | 1 |
| | 62° C. | 10 Sec | |
| | 60° C. | 10 Sec | |
| | 58° C. | 10 Sec | |
| | 56° C. | 10 Sec | |
| | 54° C. | 10 Sec | |
| | 52° C. | 10 Sec | |
| Extension | 72° C. | 1 Min | |

Note that the sequences of the oligo dT adapter primers and the like are as follows. Further, in Table 11 below, "Common" indicates that the primer is commonly used regardless of the type of transgene. In addition, "NNNNNNNN" in the "NGS-R2" sequence indicates an index tag (dual index sequence) used in the Illumina next-generation sequencer described later.

TABLE 11

| Transgene | Reverse Primer Name | reverse primer sequence (5'→3') | SEQ ID NO: |
|---|---|---|---|
| Common | Oligo-dT (23) (Oligo-dT-AD2) | [Adapter Sequence]-TTTTTTTTTTTTTTTTTTTTTTTVN | 41 |
| | Oligo-dT-AD3 | [Adapter Sequence]-TTTTTTTTTTTTTTTTTTTTTTTV | 42 |
| | Oligo-dT-AD4 | [Adapter Sequence]-TTTTTTTTTTTTTTTTTTTTTTTT | 43 |
| | ADP1-NGS-B1 | [Illumina Read 2 Primer Region]-[Adapter Sequence] | — |
| | NGS-B2 | CAAGCAGAAGACGGCATACGAGATNNNNNNNNGTGACTGGAGTTCAGACGTGTG | 44 |

Adapter Sequence - ACAGCAGGTCAGTCAAGCAGTA <SEQ ID NO: 2)

Illumina Read 2 Primer Region - GTGACTGGAGTTCAGACGTGTGCTCTTCCGATCT <SEQ ID NO: 45)

(Step 5) First Polymerase Chain Reaction (PCR)

For the amplification of double-stranded DNA, the trans-gene-specific F2 primer was added directly to the reaction solution of step 4 so as to have the composition shown in Table 12 below, and Veriti Thermal Cycler manufactured by Thermo Fisher Scientific was used to carry out the reaction under the conditions shown in Table 13 below (time required: about 35 minutes).

TABLE 12

| Reaction Component | Amount |
|---|---|
| Double-Stranded UNA Reaction Mix | 60 μL |
| 2 5 μM F2 Primer | 1.2 μL |
| Total | 61.2 μL |

TABLE 13

| PCR Condition | Temperature | Time | Cycle |
|---|---|---|---|
| Pre-Cycle Heat Denaturation | 98° C. | 30 Sec | 1 |
| Heat Denaturation | 98° C. | 10 Sec | 22 |
| Annealing | 68° C. | 10 Sec | |
| Extension | 72° C. | 30 Sec | |

(Step 6) Second PCR

The DNA amplified in step 5 was diluted 1/200, and the transgene-specific F3 primer, the adapter primer 1 (ADP1-NGS-R1), and the KOD-Plus Neo reaction solution (manu-factured by Toyobo Co., Ltd.) were mixed so as to have the composition shown in Table 14 below, and Veriti Thermal Cycler manufactured by Thermo Fisher Scientific was used to carry out the reaction under the conditions shown in Table 15 below (required time: about 40 minutes).

TABLE 14

| Reaction Component | Amount |
|---|---|
| DNA (1/200 first PCR) | 1 μl |
| KOD-Plus-Neo 10× PCR Buffer | 5 μl |
| 2 mM dNTPs | 5 μl |
| 25 mM MgSO₄ | 3 μl |
| 10 μM F3 Primer | 1.5 μl |
| 10 μM ADP1-NGS-R1 | 1.5 μl |
| KOD-Plus-Neo (1 U/μl) | 1 μl |
| H₂O | 32 μl |
| Total | 50 μl |

TABLE 15

| PCR Condition | Temperature | Time | Cycle |
|---|---|---|---|
| Pre-Cycle Heat Denaturation | 94° C. | 2 Min | 1 |
| Heat Denaturation | 98° C. | 10 Sec | 30 |
| Extension | 68° C. | 30 Sec | |

Then, the DNA was purified and primers were removed using Ampure XP (manufactured by Beckman Coulter).

Figure 2:
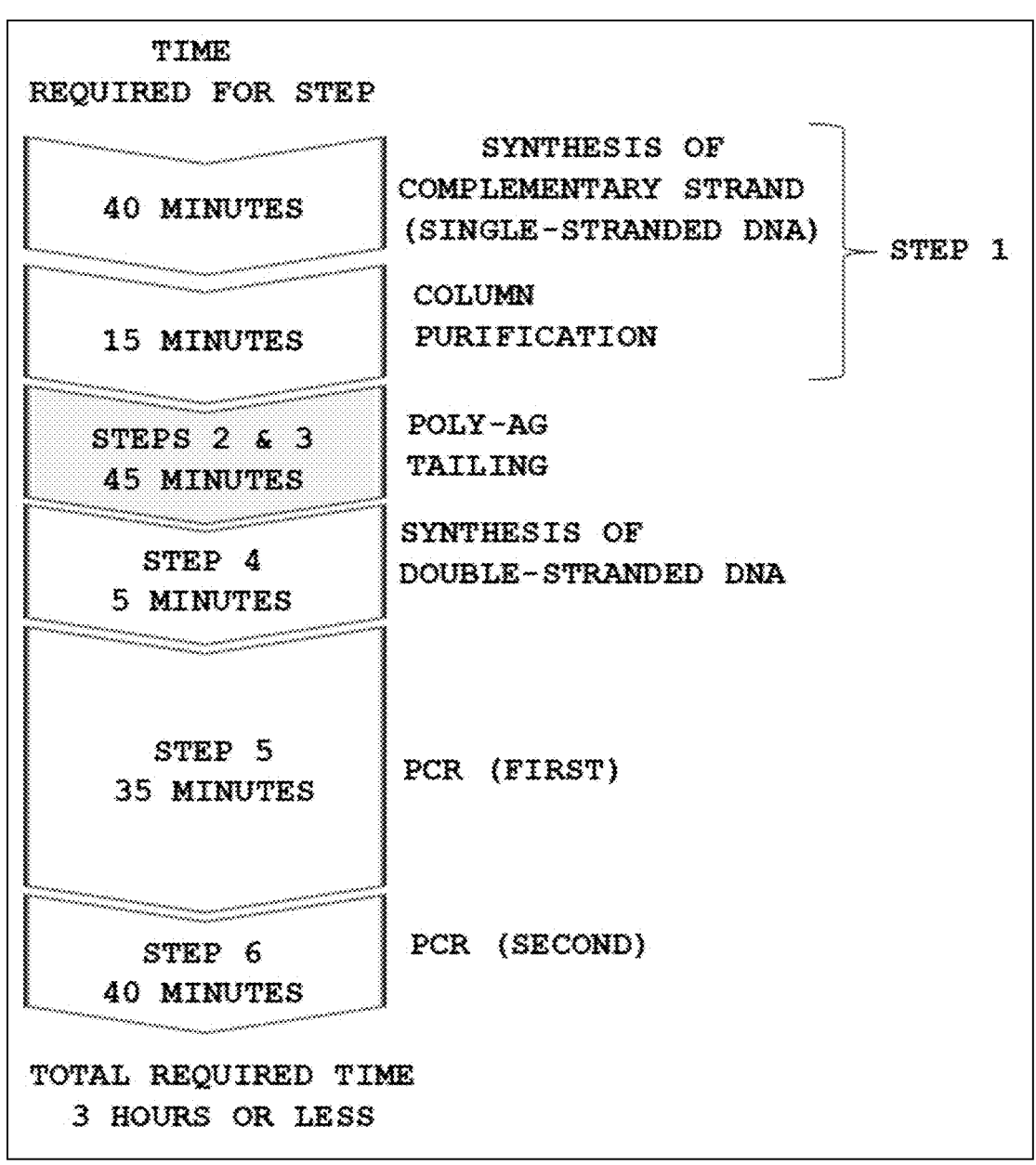
FIG. 2 is a diagram showing an example of the time required for each step in carrying out the method for amplifying a sequence adjacent to a specific sequence of the present invention.

Note that as shown in FIG. 2, the above steps were successfully performed in less than 3 hours.

(Clonality Analysis of HTLV-1 by Sanger Sequencing)

The amplification product obtained in (Step 6) above was used as a template, and the adapter-specific primer (Sanger seq primer) and BigDye Terminator v3.1 Cycle Sequencing Kit (manufactured by Thermo Fisher) were used to perform the sequence reaction, which was subjected to 3730Xl DNA Analyzer (manufactured by Thermo Fisher) to perform Sanger sequencing.

(Preparation of NGS Adapter Library)

The sequencing of the amplification product obtained in (Step 6) above, that is, the sequencing of the transgene insertion site, was performed by subjecting it to next-generation sequence analysis (NGS).

As shown in Table 16 below, 2 μL of the DNA prepared in Step 6 was used as a template and reacted under the conditions shown in Table 17 below, and the Tail-PCR method was used to prepare an amplification product (NGS adapter library) added with the Illumina next-generation sequencer adapter (index tag and flow cell binding region). In addition, after that, the DNA was purified and primers were removed using Ampure XP (manufactured by Beck-man Coulter).

TABLE 16

| Reaction Component | Amount |
|---|---|
| DNA (2nd PCR Product) | 2 μl |
| 10× Ex Taq Buffer | 2 μl |
| 2.5 mM dNTPs | 1.6 μl |
| 10 μM NGS-F2 | 1 μl |
| 10 μM NGS-R2 | 1 μl |
| Ex Taq Polymerase | 0.2 μl |
| H₂O | 12.2 μl |
| Total | 20 μl |

TABLE 17

| PCR Condition | Temperature | Time | Cycle |
|---|---|---|---|
| Pre-Cycle Heat Denaturation | 94° C. | 2 Min | 1 |
| Heat Denaturation | 94° C. | 30 Sec | 8 |
| Annealing | 60° C. | 30 Sec | |
| Extension | 72° C. | 30 Sec | |

The prepared library is subjected to Illumina Miseq for sequencing. The sequence (read) obtained by sequencing was subjected to the steps of extracting sequences with perfect matches to primer sequences by FASTX-Tool kit, trimming primer sequences and removing low precision sequences by sickle, and OTU clustering (Identity 97%) by Usearch, and a homology search was performed with BLAST+.

Example 1

The above-described method was used to analyze a mix-ture of the genomic DNA of infected cells inserted with one copy of HTLV-1 (TL-Om1) and the genomic DNA of uninfected cells (Jurkat), adjusted to each proviral level (PVL).

Figure 3:
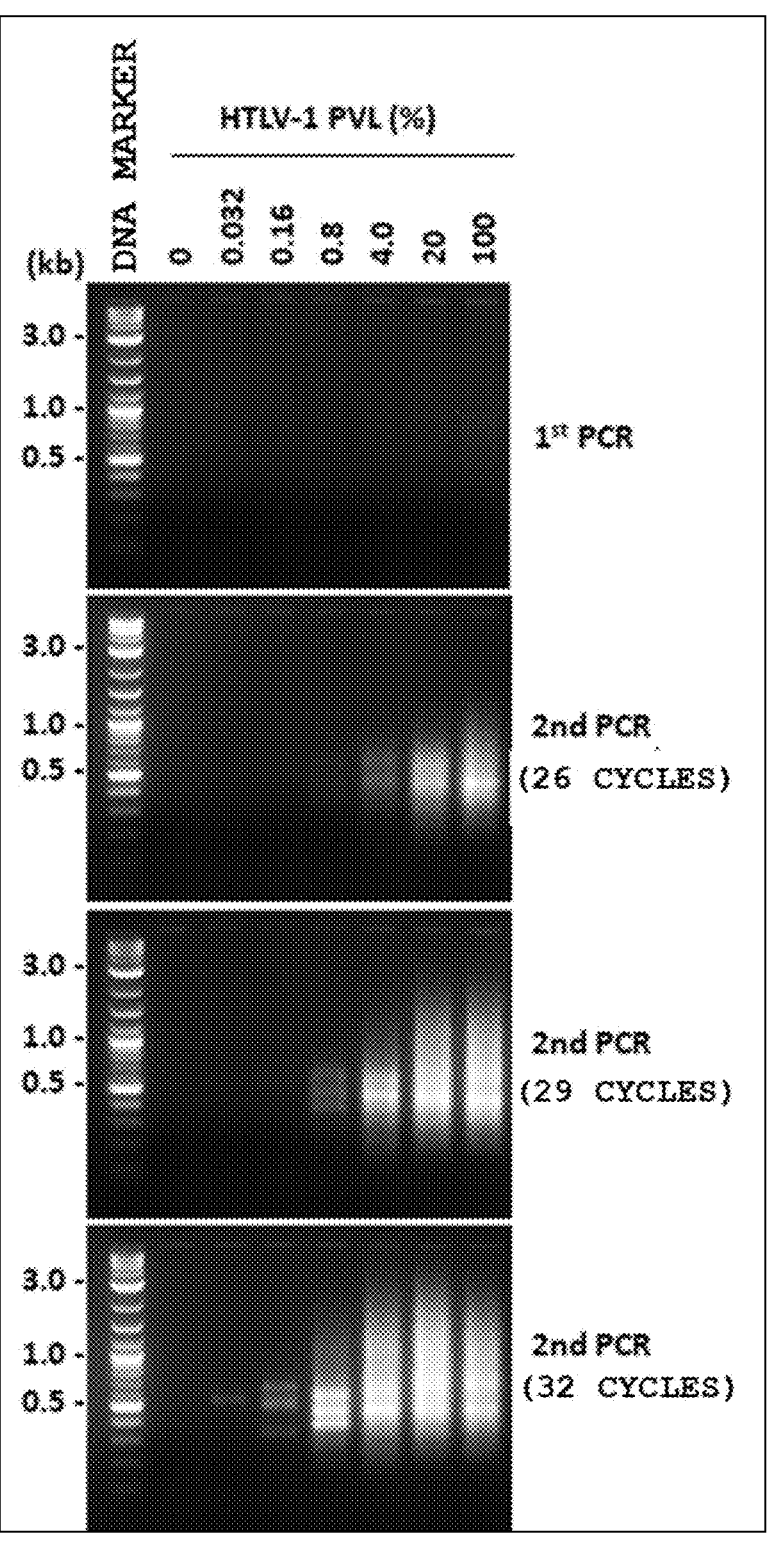
FIG. 3 provides photographs of gel electrophoresis, showing the results of using the method of the present invention to analyze a mixture of the genomic DNA of infected cells inserted with one copy of HTLV-1 (TL-Om1) and the genomic DNA of uninfected cells (Jurkat), adjusted to each proviral level (PVL) shown in the figure.

As a result, as shown in FIG. 3, specific bands were successfully detected even when the proviral level was as small as 0.032%. Specifically, according to the present invention, it has been clarified that a sequence (host genomic DNA) adjacent to a specific sequence (HTLV-1) can be specifically amplified and detected with high sensitivity.

Example 2

Figure 4:
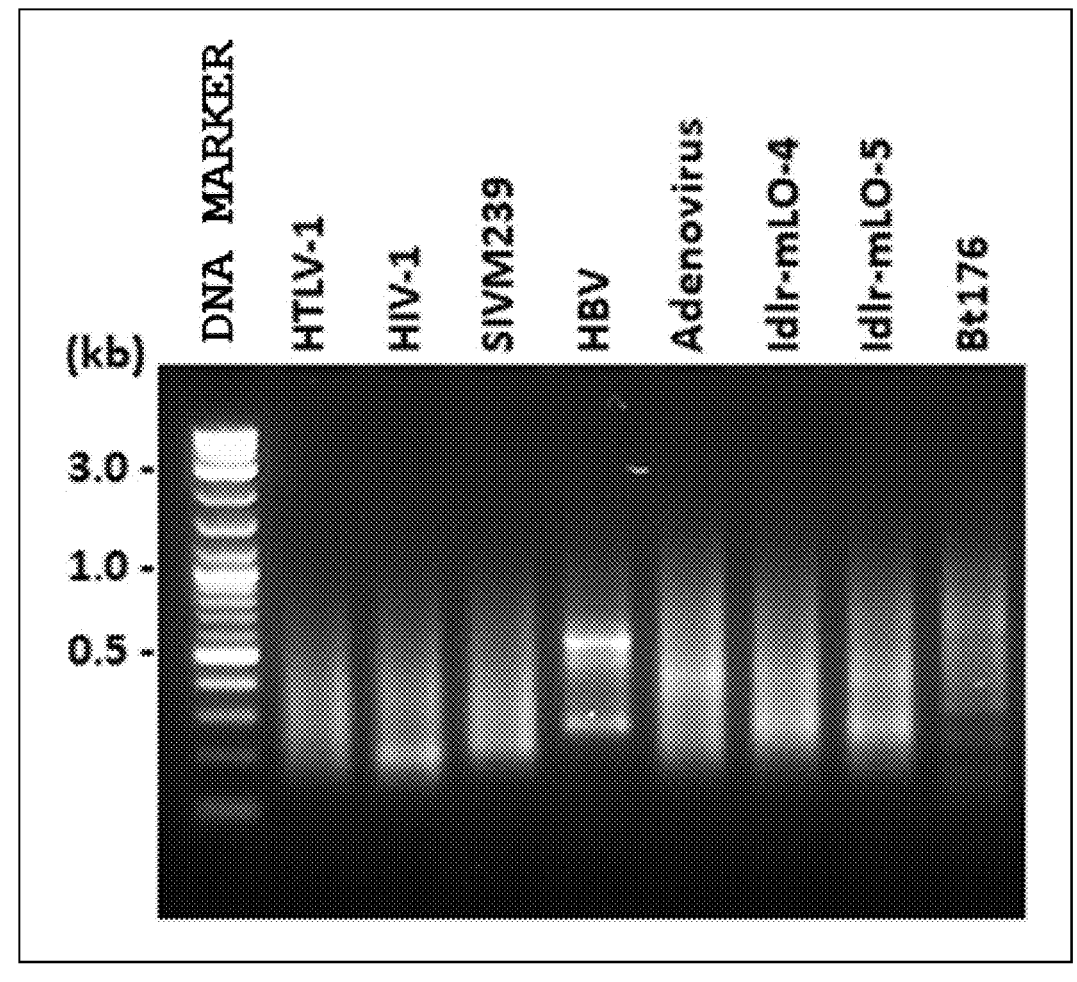
FIG. 4 provides a photograph of gel electrophoresis, showing the results of using the method of the present invention to analyze the genomic DNA of biological samples and infected cells inserted with HTLV-1, HIV-1, SIV, HBV, and adenovirus, genomic DNA of mice (idlr-mLO-4 and idlr-mLO-5) inserted with the Loxp sequence by genome editing, and genomic DNA of a genetically modified plant (Bt176).

The reaction was carried out under the same conditions as in Example 1 except that a primer for each transgene was designed and the primers were changed, and the analysis was performed. As a result, as shown in FIG. 4, it was revealed that the insertion site of foreign DNA could be specifically amplified in any of HIV-1, SIV, HBV, adenovirus, and genome-editing off-target genetically modified plant. Therefore, according to the present invention, it has been clarified that not only HTLV-1 shown in Example 1 but also the highly versatile sequence (host genomic DNA) adjacent to the specific sequence (HTLV-1) can be specifically amplified.

Example 3

Figure 5:
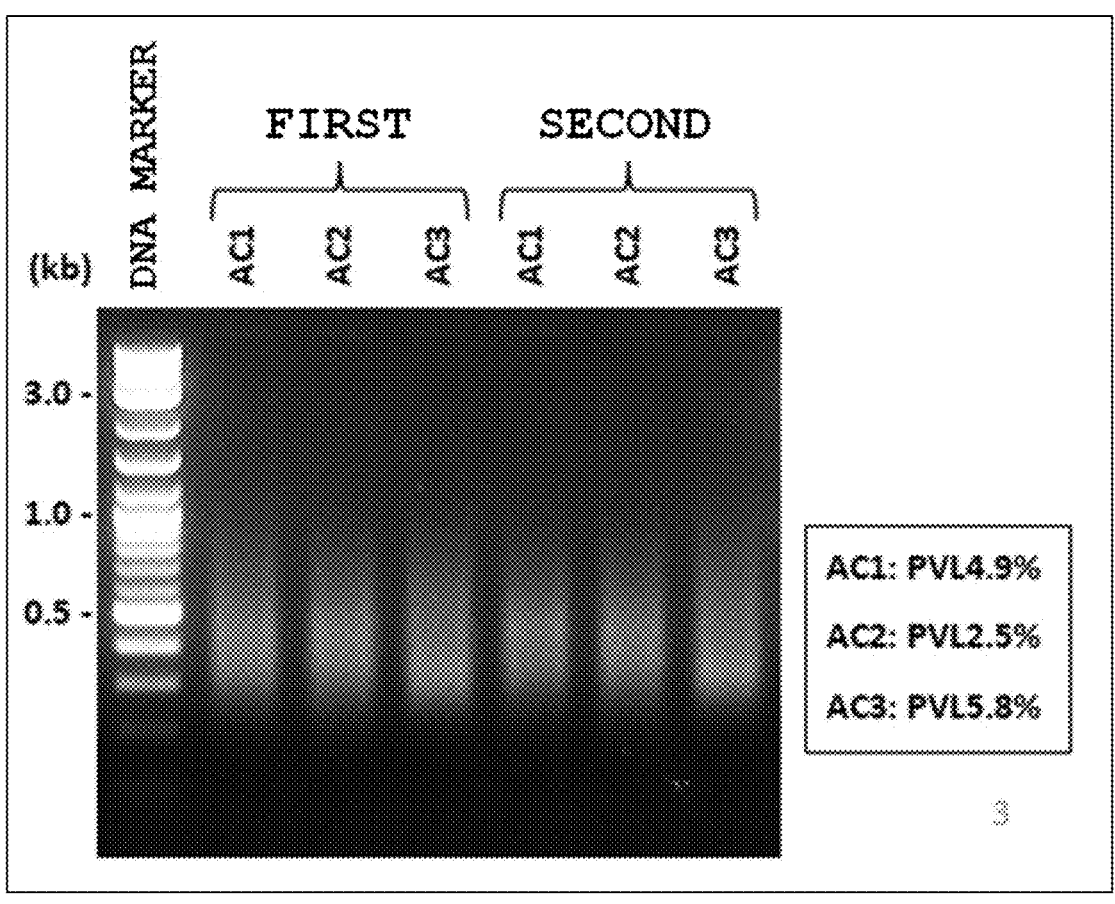
FIG. 5 is a photograph of gel electrophoresis, showing the results of two independent amplifications of the HTLV-1 insertion site on the genomic DNAs of three HTLV-1 carrier samples (AC1-3 in the figure) by the method of the present invention.

The genomic DNAs of three HTLV-1 carrier samples were used and independently reacted twice under the same conditions as in Example 1 and analyzed. As a result, as shown in FIG. 5, similar band patterns could be obtained even when the HTLV-1 insertion site was independently amplified twice for the three carrier samples. In addition, although not shown in the figure, highly reproducible data were obtained for the results of clonality analysis by Sanger sequencing and homology search in next-generation sequencing. Therefore, according to the present invention, it has been clarified that the sequence (host genomic DNA) adjacent to the specific sequence (HTLV-1) can be specifically amplified with high reproducibility.

Example 4

To clarify the technical significance of adding a second polydeoxynucleotide strand, genomic DNA of infected cells (TL-Om1) inserted with one copy of HTLV-1 was targeted for agarose gel electrophoresis analysis of the amplification product obtained in step 5 (first PCR) after performing steps 2 and 3 (polymeric addition of deoxynucleotides at the 3'-end of the complementary strand) without the addition of deoxyguanosine triphosphate (dGTP). In addition, dGTP was added to perform steps 2 and 3, which was compared with the amplification product obtained in step 5.

Figure 6:
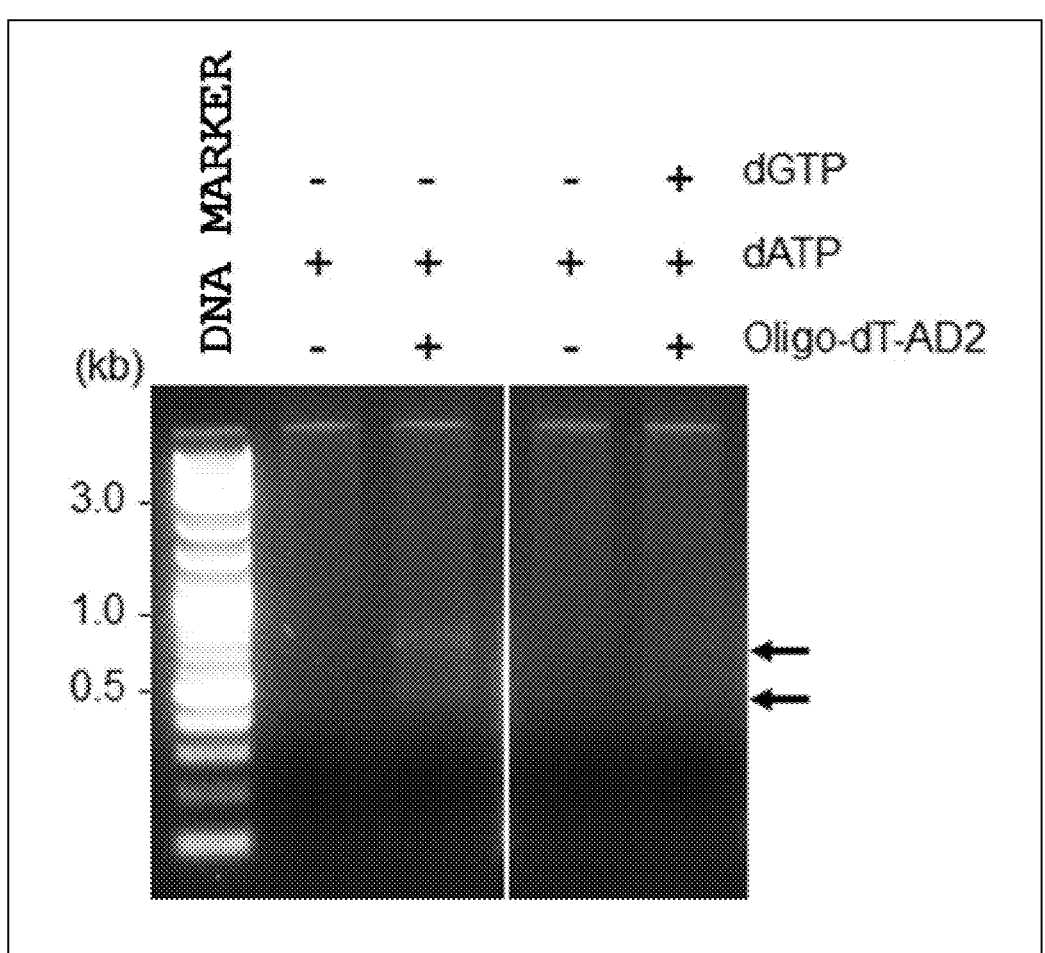
FIG. 6 is a photograph of gel electrophoresis, showing the results of agarose gel electrophoresis analysis of the amplification product obtained in step 5 (first PCR) after performing steps 2 and 3 according to the present invention (polymeric addition of deoxynucleotides at the 3'-end of the complementary strand) with or without the addition of deoxyguanosine triphosphate (dGTP).

As a result, as shown in FIG. 6, when dGTP was not added, a band derived from a non-specific amplification product was detected. On the other hand, when dGTP was added, this band was not detected. Therefore, it was clarified that it was necessary to add a second polydeoxynucleotide strand in order to specifically amplify the sequence adjacent to the specific sequence.

Example 5

To clarify the technical significance of including the fourth and fifth nucleotides in the first reverse primer, genomic DNA of infected cells (SLB1) inserted with multiple copies of HTLV-1 was targeted for agarose gel electrophoresis analysis of the amplification product obtained in step 6 (second PCR) after performing step 4 (synthesis of a double-stranded DNA) by using the one containing the fourth and fifth nucleotides (Oligo-dT-AD2), the one not containing the fifth nucleotide (Oligo-dT-AD3), and the one not containing the fourth and fifth nucleotides (Oligo-dT-AD4), with respect to the first reverse primer.

Figure 7:
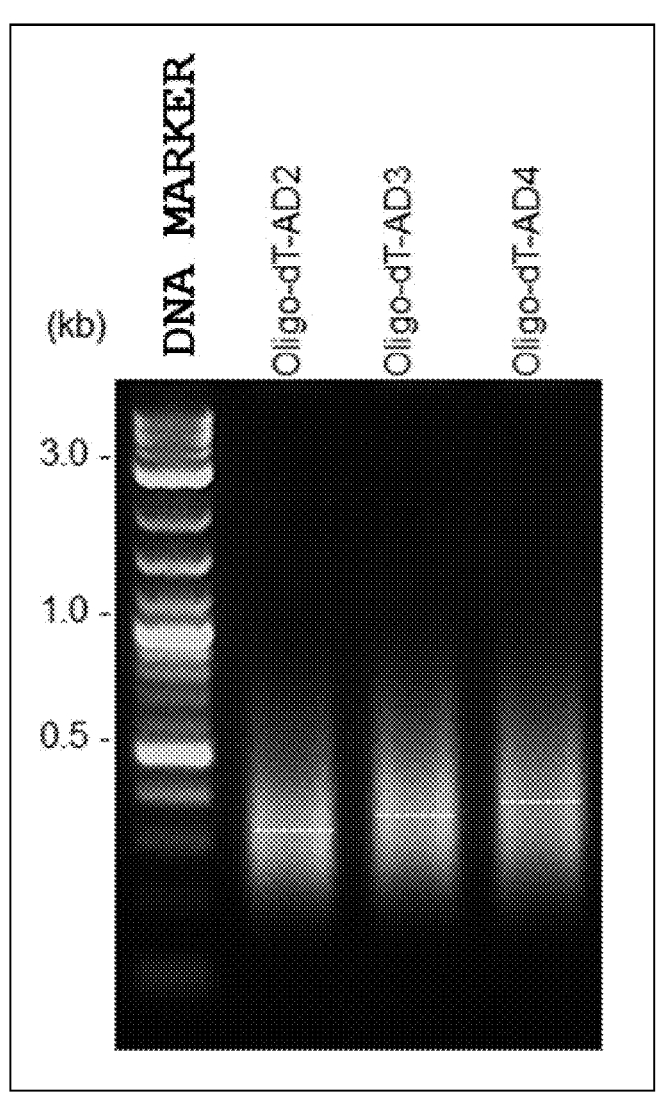
FIG. 7 is a photograph of gel electrophoresis, showing the results of agarose gel electrophoresis analysis of the amplification product obtained in step 6 (second PCR) after performing step 4 (synthesis of a double-stranded DNA) by using the one containing the fourth and fifth nucleotides (Oligo-dT-AD2), the one not containing the fifth nucleotide (Oligo-dT-AD3), and the one not containing the fourth and fifth nucleotides (Oligo-dT-AD4), with respect to the first reverse primer in the present invention. In the figure, the broken line (auxiliary line) attached to each lane indicates the position of the average length of the amplification product.

As a result, as shown in FIG. 7, it was clarified that the amplification length of the reaction product converged to the shorter chain length side in the order of Oligo-dT-AD2, Oligo-dT-AD3, and Oligo-dT-AD4. Specifically, it was revealed that by including the fourth and/or fifth nucleotide, the first reverse primer was suppressed in non-specific annealing to the first polydeoxynucleotide strand or the like accompanied by an increase in amplification length, and on the other hand, the primer was highly specifically annealed by the binding site between the sequence complementary to the adjacent sequence and the first polydeoxynucleotide strand. This suggests that the inclusion of the fourth and/or fifth nucleotide in the first reverse primer is not necessary for amplifying a sequence adjacent to a specific sequence, but is desirable in terms of increasing specificity.

Example 6

According to the method of the present invention, it has been confirmed by the method shown below that even when an RNA strand is targeted, a sequence adjacent to a specific sequence in the strand can be amplified, and further, the sequence can be determined. Specifically, in RNA encoding human TCRα (TCRA) and TCRβ (TCRB), the sequence encoding each variable region adjacent to the sequence encoding the constant region was amplified, and their sequencing was attempted.

The sequence of each primer used in Example 6 is as shown in Table 18. A Veriti Thermal Cycler manufactured by Thermo Fisher Scientific was used for temperature control in each reaction

TABLE 18

| Forward Primer Name | Forward Primer Sequence (5'→3') | SEQ ID NO: |
|---|---|---|
| TCRA-F1 | ggctgaggaagaaggtgt | 46 |
| TCRA-E2 | atgctgttgttgaaggcgtttgc | 47 |
| TCRA-F3 | [Illumina Read 1 Primer Region]-tcggtgaataggcagacagacttg | 40 |
| TCRB-F1 | gecegtagaactggacttga | 49 |
| TCRB-F2 | gctcaggcagtatctggagtca | 50 |
| TCRB-E3 | [Illumina Read 1 Primer Region]-cagtgtggccttttggatgt | 51 |

(Preparation of RNA)

Total RNA was prepared from adult T-cell leukemia/lymphoma (ATLL) cell lines (infected cells inserted with one copy of HTLV-1 (TL-Om1)) using an RNA extraction and purification kit (Quick-RNA miniprep manufactured by Zymo research) according to its accompanying protocol.

Then, in the step shown in FIG. 1, an attempt was made to amplify the sequence encoding the TCR variable region.

(Step 1) Synthesis of Complementary Strand

To synthesize the single-stranded DNA encoding the constant region and the variable region, first, the RNA was used as a template and mixed so as to have the composition shown in Table 19 below. Note that the amount of DEPC-treated water added was appropriately adjusted so that the total amount was 3.25 μL according to the amount of RNA added as a template.

TABLE 19

| Reaction Component A | Amount |
|---|---|
| RNA (10 to 1000 ng/μL) | ? μL |
| 10 μM TCRA-F1 Primer | 0.25 μL |

TABLE 19-continued

| Reaction Component A | Amount |
|---|---|
| 10 μM TCRB-F1 Primer | 0.25 μL |
| 10 mM dNTP Mix (Each 10 mM) | 0.25 μL |
| DEPC-Treated Water | ? μL |
| Total | 3.25 μL |

Then, after incubating the mixed solution of the RNA and the F1 primer and the like at 65° C. for 5 minutes, the mixture was allowed to stand on ice for at least 1 minute to anneal the RNA and the F1 primer.

Next, a mixed solution having the composition shown in Table 20 below was added, and the mixture was incubated at 54° C. for 10 minutes to synthesize the single-stranded DNA by a reverse transcription reaction.

TABLE 20

| Reaction Component B | Amount |
|---|---|
| 5× SSIV Buffer | 1 μL |
| 100 mM DTT | 0.25 μL |
| RNaseOUT ™ RNase Inhibitor (40 U/μL) | 0.25 μL |
| Superscript IV Reverse Transcriptase (200 U/μL) | 0.25 μL |
| Total | 1.75 μL |

Purification of the synthesized single-stranded DNA and removal of the F1 primer were carried out using Monarch PCR & DNA Cleanup Kit according to the attached instruction manual. Then, the single-stranded DNA once bound to the column attached to the kit was eluted by adding 9.2 μL of water, and as a result, about 8.0 μL of the sample was collected.

(Steps 2 and 3) Poly-AG Tailing at 3'-End of the Complementary Strand

PolyA tailing of the 3'-end of the single-stranded DNA described above was performed by mixing the purified single-stranded DNA (cDNA), terminal deoxytransferase (TdT) and its reaction buffer (manufactured by New England Biolabs), and dATP to the composition shown in Table 21 below and reacting at 37° C. for 30 minutes.

TABLE 21

| Reaction Component | Amount |
|---|---|
| cDNA | 8.0 μL |
| 10× TdT Buffer | 1.1 μL |
| 2.5 mM CoCl$_2$ | 1.1 μL |
| 10 mM dATP | 0.35 μL |
| TdT (20 U/μL) | 0.25 μL |
| RNase H | 0.20 μL |
| Total | 11 μL |

Then, dGTP was added so as to have the composition shown in Table 22 below, which was further reacted at 37° C. for 15 minutes to add poly AG to the 3'-end of the single-stranded DNA.

TABLE 22

| Reaction Component | Amount |
|---|---|
| PolyA Tail-Added cDNA | 11 μL |
| 10× TdT Buffer | 0.1 μL |
| 2.5 mM CoCl$_2$ | 0.1 μL |
| 10 mM dGTP | 0.35 μL |
| H$_2$O | 0.45 μL |
| Total | 12 μL |

Then, the terminal deoxytransferase was inactivated by heat treatment at 75° C. for 10 minutes.

(Step 4) Synthesis of Double-Stranded DNA

For the synthesis of double-stranded DNA, an oligo dT adapter primer (Oligo-dT-AD2) and Q5 Hot Start High-Fidelity DNA Polymerase reaction solution (manufactured by New England Biolabs) were added directly to the reaction solution of step 3 described above so as to have the composition shown in Table 23 below, and the reaction was caried out under the touchdown conditions shown in Table 24 below. Note that the obtained sample was maintained at 4° C. until the next step was started.

TABLE 23

| Reaction Component | Amount |
|---|---|
| PolyAG Tail-Added cDNA | 12 μL |
| 5× Q5 Reaction Buffer | 12 μL |
| 10 mM dNTPs | 1.2 μL |
| 10 μM oligo-dT-AD2 | 3 μL |
| Q5 HS-High-Fidelity DNA Polymerase (2 U/μL) | 0.6 μL |
| H$_2$O | 31.2 μL |
| Total | 60 μL |

TABLE 24

| PCR Condition | Temperature | Time | Cycle |
|---|---|---|---|
| Heat Denaturation | 70° C. | 2 Min | 1 |
| Annealing | 64° C. | 10 Sec | 1 |
| | 62° C. | 10 Sec | |
| | 60° C. | 10 Sec | |
| | 58° C. | 10 Sec | |
| | 56° C. | 10 Sec | |
| | 54° C. | 10 Sec | |
| | 52° C. | 10 Sec | |
| Extension | 72° C. | 1 Min | |

(Step 5) First Polymerase Chain Reaction (PCR)

For the amplification of double-stranded DNA, the F2 primer mix specific to each constant region of TCRA and TCRB was directly added to the reaction solution of step 4 so as to have the composition shown in Table 25 below, and the reaction was carried out under the conditions shown in Table 26 below.

TABLE 25

| Reaction Component | Amount |
|---|---|
| Double-Stranded DNA Reaction Mix | 60 μL |
| 25 μM TCRA-TCRB-F2 Primer Mix | 1.2 μL |
| Total | 61.2 μL |

TABLE 26

| PCR Condition | Temperature | Time | Cycle |
|---|---|---|---|
| Pre-Cycle Heat Denaturation | 98° C. | 30 Sec | 1 |
| Heat Denaturation | 98° C. | 10 Sec | 20 |
| Annealing | 65° C. | 15 Sec | |
| | 62° C. | 15 Sec | |
| Extension | 72° C. | 30 Sec | |

(Step 6) Second PCR

The DNA amplified in step 5 was diluted 1/200, and the F3 primer specific to each constant region of TCRA and TCRB, the adapter primer 1 (ADP1-NGS-R1), and the KOD-Plus Neo reaction solution (manufactured by Toyobo Co., Ltd.) were mixed so as to have the composition shown in Table 27 below, and the reaction was carried out under the conditions shown in Table 28 below.

TABLE 27

| Reaction Component | Amount |
|---|---|
| DNA (1/200 of first PCR) | 1 μL |
| 10× PCR Buffer for KOD-Plus-Neo | 2.5 μL |
| 2 mM dNTPs | 2.5 μL |
| 25 mM MgSO₄ | 1.5 μL |
| 10 μM TCRA-F3 Primer or TCRB-F3 Primer | 0.75 μL |
| 10 μM ADP1-NGS-R1 | 0.75 μL |

TABLE 27-continued

| Reaction Component | Amount |
|---|---|
| KOD-Plus-Neo (1 U/μL) | 0.5 μL |
| H₂O | 15.5 μL |
| Total | 25 μL |

| PCR Condition | Temperature | Time | Cycle |
|---|---|---|---|
| Pre-Cycle Heat Denaturation | 94° C. | 2 Min | 1 |
| Heat Denaturation | 98° C. | 10 Sec | 30 |
| Annealing | 65° C. | 30 Sec | |
| Extension | 68° C. | 30 Sec | |

Then, the DNA was purified and primers were removed using Ampure XP.

(TCR Repertoire Analysis by Sanger Sequencing)

The amplification product obtained in (Step 6) above was used as a template, and the adapter-specific primer (Sanger seq primer) and BigDye Terminator v3.1 Cycle Sequencing Kit (manufactured by Thermo Fisher) were used to perform the sequence reaction, which was subjected to 3730Xl DNA Analyzer (manufactured by Thermo Fisher) to perform Sanger sequencing. Then, each obtained sequence was collated with the database of V-QUEST. As a result, as shown in Tables 29 and 30, the results of the rearrangement of the a gene and the R gene were successfully identified (note that Table 29 shows the results of the rearrangement analysis of the human TCRA gene, and Table 30 shows the results of the rearrangement analysis of the human TCRB gene).

TABLE 29

| Result summary: | Productive TRA rearranged sequence (no stop codon and in-frame junction) | | |
|---|---|---|---|
| V-GENE and allele | Homsap TRAV12-1*01 F | score = 1306 | identity = 99.62% (263/264 nt) |
| J-GENE and allele | Homsap TRAJ27*01 F | score = 270 | identity = 100.00% (54/53 nt) |
| FR-IMGT lengths, CDR-IMGT lengths and AA JUNCTION | (26.17.33.11) | [6.6.10] | CAVNTNAGKSTF |

TABLE 30

| Result summary: | Productive TRB rearranged sequence (no stop codon and in-frame junction) | | |
|---|---|---|---|
| V-GENE and allele | Homsap TRBV6-5*01 F score = 1351 | | identity = 99.63% (272/273 nt) |
| J-GENE and allele | Homsap TRBJ2-1*01 F score = 250 | | identity = 100.00% (50/50 nt) |
| D-GENE and allele by IMGT/JunctionAnalysis | Homsap TRBD2*01 F | | D-REGION is in reading frame 1 |
| FR-IMGT lengths, CDR-IMGT lengths and AA JUNCTION | [26.17.37.10] | [5.6.12] | CASRETSSYNEQFF |

INDUSTRIAL APPLICABILITY

As described above, according to the present invention, it is possible to amplify a sequence adjacent to a specific sequence in a short time with high efficiency, high sensitivity, low cost, high versatility, and good reproducibility, and to even determine the sequence.

Therefore, since the present invention is excellent in identifying the insertion site (adjacent sequence) of foreign DNA (specific sequence) into the host genome in gene modification technologies such as gene therapy and genome editing, as well as in virus-related diseases, it is extremely useful in evaluating the safety of gene modification technologies and in developing diagnostic and therapeutic methods for virus-related diseases. The present invention is also extremely useful in TCR repertoire analysis, as described above.

The invention claimed is:

1. A method for amplifying a sequence adjacent to a specific sequence in a nucleotide strand, comprising the following steps (1) to (6):

(1) a step of annealing a first forward primer to the specific sequence, performing an extension reaction with the first forward primer as a starting point, and synthesizing a complementary strand containing a sequence complementary to an adjacent sequence at a 3-end;

(2) a step of polymerically adding a first deoxynucleotide to the 3-end of the complementary strand obtained in step (1);

(3) a step of further polymerically adding a second deoxynucleotide to a 3'-end of a polydeoxynucleotide strand comprising the first deoxynucleotide added in step (2);

(4) a step of annealing a first reverse primer to a site spanning a junction of the 3'-end of the complementary strand and the polydeoxynucleotide strand in a single-stranded DNA formed in step (3), performing an extension reaction with the first reverse primer as a starting point, and synthesizing a double-stranded DNA;

(5) a step of performing a polymerase chain reaction with the double-stranded DNA synthesized in step (4) as a template by using a second forward primer complementary to the specific sequence and the first reverse primer; and (6) a step of further performing a polymerase chain reaction with an amplification product obtained in step (5) as a template by using a third forward primer complementary to the specific sequence and a second reverse primer, wherein the second forward primer is located closer to the adjacent sequence than the first forward primer in the specific sequence, the third forward primer is located closer to the adjacent sequence than the second forward primer in the specific sequence, the first reverse primer is a primer containing an adapter primer sequence and an oligonucleotide comprising a third deoxynucleotide in order from a 5'-end, the second reverse primer is a primer containing an adapter primer sequence at a 3'-end, the first to third deoxynucleotides are each one type of deoxynucleotide selected from four types consisting of deoxyadenosine, deoxyguanosine, deoxycytidine, and deoxythymidine, the second deoxynucleotide is a deoxynucleotide different from the first deoxynucleotide, and the third deoxynucleotide is a deoxynucleotide complementary to the first deoxynucleotide.

2. A method for determining a sequence adjacent to a specific sequence in a nucleotide strand, comprising the steps of:

amplifying the adjacent sequence by the method according to claim 1; and performing sequence analysis on the amplified adjacent sequence.

3. The method according to claim 1, wherein the first reverse primer is a primer containing an adapter primer sequence, an oligonucleotide comprising the third deoxynucleotide, a fourth deoxynucleotide, and a fifth deoxynucleotide in order from the 5'-end, the fourth deoxynucleotide is a deoxynucleotide randomly selected from three types of deoxynucleotide other than the type of the third deoxynucleotide, and the fifth deoxynucleotide is a deoxynucleotide randomly selected from the four types of deoxynucleotide.

4. The method according to claim 1, wherein the specific sequence is a sequence derived from a foreign gene inserted in a DNA strand, and the adjacent sequence is a sequence derived from a host genome adjacent to the foreign gene inserted in the DNA strand.

5. A kit for use in the method according to claim 1, comprising: the first forward primer; the second forward primer; the third forward primer; the first reverse primer; and the second reverse primer.

\* \* \* \* \*